US006812337B1

(12) United States Patent
St. George-Hyslop et al.

(10) Patent No.: US 6,812,337 B1
(45) Date of Patent: Nov. 2, 2004

(54) PRESENILIN ASSOCIATED MEMBRANE PROTEIN AND USES THEREOF

(75) Inventors: Peter St. George-Hyslop, Toronto (CA); Paul E. Fraser, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 09/541,094

(22) Filed: Mar. 31, 2000

Related U.S. Application Data

(60) Provisional application No. 60/173,826, filed on Dec. 30, 1999, and provisional application No. 60/127,452, filed on Apr. 1, 1999.

(51) Int. Cl.$^7$ .......................... C07H 21/04; C12P 21/06; C12P 21/04; C12N 5/00
(52) U.S. Cl. ..................... 536/23.5; 435/325; 435/69.1; 435/70.1
(58) Field of Search .............................. 536/23.1, 23.5; 435/69.1, 325, 252.3, 320.1

(56) References Cited

U.S. PATENT DOCUMENTS

| 5,986,054 A | 11/1999 | St. George-Hyslop et al. |
| 6,020,143 A | 2/2000 | St. George-Hyslop et al. |

FOREIGN PATENT DOCUMENTS

| WO | WO 96/34099 A3 | 10/1996 |

OTHER PUBLICATIONS

Nomura, Accession No. D87442, 1997.*
Levinson; Medical Microbiology & Immunology, 1994, Immunity 57:292–293.*
Huang et al. "Depression of human embryonic . . . " PNAS 95:14669–14674 (1998).*
Ngo et al. "Computational complexity, protein . . . " in The Protein Folding Problem and Tertiary Structure Prediction, Merz et al. (eds.), Birkhauser Boston: Boston, MA, pp. 433 and 492–495 (1994).*
Rudinger "characteristics of the amino acids . . . " in Peptide Hormones, Parsons (ed.), University Park Press: Baltimore, MD, pp. 1–7 (1976).*
Borchelt et al., Neuron, 1996; 17:1005–1013.
Buxbaum et al., Proc. Natl. Acad. Sci. USA, 1990; 87:6003–6007.
Citron et al., Nature Med., 1997; 3:67–72.
De Stropper et al., J. Biol. Chem., 1997; 272:3590–3598.
De Stropper et al., Nature, 1999; 398:518–522.
De Stropper et al., Nature, 1998; 391:387–390.
Doan et al., Neuron, 1996; 17:1023–1030.
Duff et al., Nature, 1996; 383:710–713.
Green et al., Mech. Dev., 1998; 73:59–72.
Kehoe et al., Hum. Mol. Genet., 1999; 8:237–245.
Lehmann et al., J. Biol. Chem., 1997; 272:12047–12051.
Levesque et al., J. Neurochem., 1998: 72:999–1008.
Levitan et al., Nature, 1995; 377:351–354.
Levy–Lehad et al., Science, 1995; 269:970–973.
Li et al., Cell 1997; 90:917–927.
Martin et al., NeuroReport, 1995; 7:217–220.
Nishimura et al., Nature Med. 1999;5:164–169.
Paffenholtz et al., Differentiation, 1997; 61:293–304.
Paffenholtz et al., Exp. Cell Res., 1999; 250:452–464.
Rogaev et al., Nature, 1995; 376:775–778.
Scheuner et al., Nature Med., 1996; 2:864–870.
Seeger et al., Proc. Natl. Acad. Sci., 1997; 94:5090–5094.
Shen et al., Cell, 1997; 89:629–639.
Jones SJM, "Hypothetical 81.4 kd protein zc434–6," GenBank Accession No. Q23316, Jul. 15, 1998.
Nagase T. et al., "Human mRNA for KIAA0253 gene," GenBank Accession No. D87442, No. D87442, Nov. 9, 1996.
Nagase T. et al., "Hypothetical protein KIAA0253," GenBank Accession No. Q92542.
International Search Report (PCT/CA00/00354).
Sherrington et al., Nature, 1995: 375–:754–760.
Song et al., Proc. Natl. Acad. Sci. USA, 1999; 96:6959–6963.
Struhl et al., Nature, 1999; 398:522–525.
Underhill et al., Genomics, 1999; 55:185–193.
Walter et al., Molec. Medicine, 1996; 2:673–691.
Wilson et al., Nature, 1994; 368:32–38.
Wolozin et al., Science, 1996; 274:1710–1713.
Wong et al., Nature, 1997; 387:233–292.
Ye et al., Nature, 1999; 398:525–529.
Yu et al., J. Biol. Chem., 1998; 273:16470–16475.
Boulianne et al., Neuro. Report (Fast Track), 1997; 8:1025–1029.
Zhou et al., Neuro. Report, 1997; 8:2085–2090.

\* cited by examiner

*Primary Examiner*—Deborah J. Reynolds
*Assistant Examiner*—Joseph Woitach
(74) *Attorney, Agent, or Firm*—Darby & Darby

(57) ABSTRACT

Presenilin Associated Membrane Protein (PAMP), and nucleic acids encoding this protein, are provided. PAMP and PAMP nucleic acids provide diagnostic and therapeutic tools for evaluating and treating or preventing neurodegenerative diseases. In a specific embodiment, mutations in PAMP are diagnostic for Alzheimer's Disease or spina bifida. The invention further relates to screening, particularly using high-throughput screens and transgenic animal models, for compounds that modulate the activity of PAMP and presenilins. Such compounds, or gene therapy with PAMP, can be used in treating neurodegenerative diseases, particularly Alzheimer's Disease. In addition, the invention provides PAMP mutants, nucleic acids encoding for PAMP mutants, and transgenic animals expressing PAMP mutants, which in a preferred aspect result in biochemical changes similar to those induced by mutations in βAPP, PS1, or PS2, associated with familial Alzheimer's disease.

14 Claims, 2 Drawing Sheets

```
Hum:    1   MATAGGGSGADPGSRGLLRLLSFCVLLAGLCRGNSVERKIYIPLNKTAPCVRLLNATHQI   60
Mou         MAT GGSG DPGSRGLL LLSF V+LAGLC GNSVERKIYIPLNKTAPCVRLLNATHQI
Dros:   1                   A + +G     K+Y P+   A C R LN THQ
C.ele   L                 +++AG+C G S +    +++    C R N TH+

Hum:   61   GCQSSISGDTGVIHVVEKEEDLQWVLTDGPNPPYMVLLESKHFTRDLMEKLKGRTSRIAG  120
Mou         GCQSSISGDTGVIHVVEKEEDL+WVLTDGPNPPYMVLLE K FTRD+MEKLKG TSRIAG
Dros        GC S+ SG   GV+H++   E DL+++L+  P+PPY ++      FTR+ +  +LK
C.eleg      GCQ++    + G+I ++K+ED +       W + Y LL        RD +  +LK  +  ++G Hum:  121   LAVSLTKPSPASGFSPSVQCPNDGFGVYSNSYGPEFAHCREIQWNSLGNGLAYEDFSFPI  180
Mou         LAV+L KP+  S FSPSVQCPNDGFG YSNSYGPEFAH ++   WN LG GLAYED SFPI
Dros        + + +++    FS  + CPN    G+ S  S      +++  +  WN  G GL +EDF FPI
C.eleg      ++S      ++ S     +CPN      Y          E+       E + NS G+GL  D+    +

Hum:  181   FLLEDENETKVIKQCYQDHNLSQNGSAPTFPLCAMQLFSHMHAVISTATCMRRSSIQSTF  240
Mou         FLLEDE+ETKVIKQCYQDHNL QNGSAP+FPLCAMQLFSHMHAVISTATCMRRS IQSTF
Dros :      + + D ++  +++C+QD N    +       LCA+++  S M A ++T   CMRR++  +
C.eleg      +++ +  + +I+++CY    N  +    +     +PC K       A ++ C RR     + F Hum:  241   SINPEIVCDPLSDYNVWSMLKPINTTGTLKPDDRVVVAATRLDSRSFF-WNVAPGAESAV  299
Mous        SINPEIVCDPLSDYNVWSMLKPINT+  L+PD RVVVAATRLDSRSFF WNVAPG ESAV
Dros        ++   CDPL    NV     P +T  T+  +++ ++     RLD+ +    + F   V  GA ++
C.eleg      +N + +C   +  N+++      PI T+ T+ +   +  +++          R+DS        ++  G  S  +

Hum:  300   ASFVTQLAAAEALQKAPDVTTLPRNVMFVFFQGETFDYIGSSRMVYDMEKGKFPVPVQLENV  359
Mou         ASFVTQLAAAEAL KAPDVTTL RNVMFVFFQGETFDYIGSSRMVYDME GKFPV+LEN+
Dros        F   A LQ P  +   NV+FV F GE++DYIGS R VYDMEK +Fp+  +N+
C.eleg      S ++ LAAA ++/QKA + +   RNV F FF GE+ DYIGS    Y ME GKFp++    +
```

Figure 1A

```
Hum  : 360  DSFVELGQVALRTSLELMWHTDPVSQKNESVRNQVEDLLATLEKSGAGVPAVILRRPNQS 419
Mou         DSFVELGQVALRTSL+LMWHTDP+SQKNESV+NQVEDLLATLEKSGAGVP V+LRR QS
Dros        D  +++G +   +++L       ++  Q++L    KS   G   I +   S
C.eleg      D  +E+ Q+ +  + +++H D   ++ +  + Q +++   +E+ G    A   L +P+ S Hum  : 420  QPLPPSSLQRFLRARNISGVVLADHSGAFHNKYYQSIYDTAENINVSYPEWLSPEEDLNF 479
Mou         Q  PPSSLQRFLRARNISGVVLADHSG+FHN+YYQSIYDTAENINV+YPEW S EEDLNF
Dros            LPP+S Q FLR  N + ++L   +    NKYY S YD A+N++ +Y        L
C.eleg      +PP+S   F +A ++ V+LA ++   +    S:D          EW    E +

Hum  : 480  VTDTAKALADVATVLGRALYELAGGTMFSDTVQADPQTVTRLLYGFLIKANNSWFQSILR 539
Mou         VTDTAKALA+VATVL RALYELAGGTNFS  ++QADPQTVTRLLYGFL++ANNSWPQSIL+
Dros        V D   DV++++ ALY+   G   ++ T A+F         LY FL  A+    F++
C.eleg          ++  V+T +   A  + G          +D ++T ++ LI +N WF Hum  : 540  QDLRSYLGDGPLQHYIAVSSPTNTTYVQYALANLTGTVNLTREQCQDPSKVPSENKDL 599
Mous        DLRSYL D PLQHYIAVSSPTNTTYVVQYAL NLTG    NLTREQCQDPSKVP+E+KDL
Dros          S L + P  YI+V   +  +    Y L     L+    ++ R+ C D
C.eleg      Q L SY G     YI++ SPT    ++ +AL + T+     ++ C     +     +

Hum: 600    YEYSWVYQGPLHSNETDRLPRCVRSTARLARALSPAFELSQWSSTEYSTWTESRWKDIRAR 659
Mous        YEYSWVQGP +SN T+RLP+CVRST  RLARALSPAFELSQNSSTEYSTW ESRWKDI+AR
Dros        PLH       + + C  +T    +  LLSPAF +   WSS   YSTWTES W       AR
C.eleg      Y Y+W  P  N +         C++S           +SPA + +  +T YSTW ES +

Hum: 660    IFLIASKELELITLTVGFGILIPSLIVTYCINAKADVLFIAPREPGAVSY 709
Mous        IFLIASKELE ITL VGF  L+FSLIVTYCINAKADVLF+APREPGAVSY
Dros        IFL  S  ++ TL+VG  +LI  S  + Y I++++++VLF
C.eleg      ++L+    E  +++       +I +L+ ++   ++    FI    EP A
```

Figure 1B

SEQUENCE LISTING

<160> NUMBER OF SEQ ID NOS: 19

<210> SEQ ID NO 1
<211> LENGTH:
<212> TYPE:
<213> ORGANISM:

<400> SEQUENCE: 1

This Sequence is intentionally skipped

<210> SEQ ID NO 2
<211> LENGTH:
<212> TYPE:
<213> ORGANISM:

<400> SEQUENCE: 2

This Sequence is intentionally skipped

<210> SEQ ID NO 3
<211> LENGTH: 422
<212> TYPE: DNA
<213> ORGANISM: mouse

<400> SEQUENCE: 3

```
cccagcggag aggcaagatg gctacgacta ggggcggctc tgggcctgac ccaggaagtc      60
ggggtcttct tcttctgtct ttttccgtgg tactggcagg attgtgtggg ggaaactcag     120
tggagaggaa aatctacatt cccttaaata aaacagctcc ttgtgtccgc ctgctcaacg     180
ccactcatca gattggctgc cagtcttcaa ttagtgggga tacaggggtt atccatgtag     240
tggagaaaga agaagactga agtgggtgtt gacgatggcc ccaaccccct tacatggtct     300
gctggaggga agtcttcaca gagatgtaat ggagaagctg aggacaacag tagatcctgg     360
tcttgccgtg attagcagcc actcacttaa gtttctctag tgtgagtgcc aatgatgggt     420
tt                                                                    422
```

<210> SEQ ID NO 4
<211> LENGTH: 473
<212> TYPE: DNA
<213> ORGANISM: unknown
<220> FEATURE:
<223> OTHER INFORMATION: EST from unknown organism

<400> SEQUENCE: 4

```
tggagaggaa aatctacatt cccttaaata aaacagctcc ttgtgtccgc ctgctcaacg      60
ccactcatca gattggctgc cagtcttcaa ttagtgggga tacaggggtt atccatgtag     120
tggagaaaga agaagacctg aagtgggtgt tgaccgatgg ccccaacccc ccttacatgg     180
ttctgctgga gggcaagctc ttcaccagag atgtaatgga agctgaag ggaacaacca      240
gtagaatcgc tggtcttgcc gtgactctag ccaagcccaa ctcaacttca gcttctctc     300
ctagtgtgca gtgcccaaat gatgggtttg gtaattactc caactcctac gggccagagt     360
ttgctcactg gaagaaaaca ctgtggaatg aactcggcaa aggcttggct tatgaagacc     420
ttagtttccc caatcttcct cctggagatg aggaccgaaa caaggtcatc aag           473
```

<210> SEQ ID NO 5
<211> LENGTH:
<212> TYPE:
<211> LENGTH:

```
<212> TYPE:
<213> ORGANISM:

<400> SEQUENCE: 5

This Sequence is intentionally skipped

<210> SEQ ID NO 6
<211> LENGTH: 463
<212> TYPE: DNA
<213> ORGANISM: unknown
<220> FEATURE:
<223> OTHER INFORMATION: EST from unknown organism

<400> SEQUENCE: 6
gggctcgaaa catctctggc gtggtcctgg ctgaccactc tggctccttc cacaatcggt      60
attaccagag catttatgac acggctgaga acattaatgt gacctatcct gagtggcaga     120
gccatgaaga ggacctcaac tttgtgacag acactgccaa ggcactggcg aatgtggcca     180
cagtgctggc gcgtgcactg tatgagcttg caggaggaac caacttcagc agctccatcc     240
aggctgatcc ccagacagtt acacgtctgc tctatgggtt cctggttaga gctaacaact     300
catggtttca gtcgatcctg aaacatgacc taaggtccta tttggatgac aggcctcttc     360
aacactacat cgccgtctcc agccctacca cacgactta cgttgtgcag tacgccttgg      420
caaacctgac tgggcaaggc gaccaacctc acccgagagc agt                       463

<210> SEQ ID NO 7
<211> LENGTH: 481
<212> TYPE: DNA
<213> ORGANISM: unknown
<220> FEATURE:
<223> OTHER INFORMATION: EST from unknown organism

<400> SEQUENCE: 7
gaggacctca actttgtgac agacactgcc aaggcactgg cgaatgtggc cacagtgctg      60
gcgcgtgcac tgtatgagct tgcaggagga accaacttca gcagctccat ccaggctgat     120
ccccagacag ttacacgtct gctctatggg ttcctggtta gagctaacaa ctcatggttt     180
cagtcgatct tgaaacatga cctaaggtcc tatttggatg acaggcctct tcaacactac     240
atcgccgtct ccagccctac caacacgact tacgttgtgc agtacgcctt ggcaaacctg     300
actggcaagg cgaccaacct cacccgagag cagtgccagg atccaagtaa agtcccaaat     360
gagagcaagg atttatatga atactcgtgg gtacaaggcc cttggaattc aacaggaca      420
gagaggctcc acagtgtgt gcgctcacag tgcgactggc aagggcttgt ccctgccttt      480
g                                                                     481

<210> SEQ ID NO 8
<211> LENGTH: 398
<212> TYPE: DNA
<213> ORGANISM: unknown
<220> FEATURE:
<223> OTHER INFORMATION: EST from unknown organism

<400> SEQUENCE: 8
agagctaaca actcatggtt tcagtcgatc ttgaaacatg acctaaggcc tatttggatg      60
acaggcctct tcaacactac atcgccgtct ccagccctac caacacgact tacgttgtgc     120
agtacgcctt ggaaacctga ctggcaaggc gaccaacctc acccgagagc agtgccagga     180
tccaagtaaa gtcccaaatg agagcaagga tttatatgaa tactcgtggg tacaaggccc     240
```

```
ttggaattcc aacaggacag agaggctccc acagtgtgtg cgctccacag tgcgactggc      300
cagggccttg tccctgcct ttgaactgag tcagtggagc tccacagaat actctacgtg       360
ggcggagagc cgctggaaag acatccaagc tcggatat                              398

<210> SEQ ID NO 9
<211> LENGTH: 172
<212> TYPE: DNA
<213> ORGANISM: unknown
<220> FEATURE:
<223> OTHER INFORMATION: EST from unknown organism

<400> SEQUENCE: 9
tgtgcgctcc acagtgcgac tggccagggc gttgtcacct gcctttgaac tgagtcagtg      60
gagctccaca gaatactcta cgtgggcgga gagcgcgtgg aaagacatcc cagctcggat     120
attcctaatt gccagcaaag agcttgagtt catcacgctg atcgtgggct tc             172

<210> SEQ ID NO 10
<211> LENGTH: 425
<212> TYPE: DNA
<213> ORGANISM: unknown
<220> FEATURE:
<223> OTHER INFORMATION: EST from unknown organism

<400> SEQUENCE: 10
tttttttttt tttttgtat tgcataattt taatgaaact tgctatttat atacttacaa       60 aaaaaaaaa aaggaaaaa accccaacaa aaatagataa ttatagttta ataataaaaa       120
gtacaactga gcactgtggg ctggaggtgg atacccact aacagcgtg cccacactaa      180 catgccatct gcacacctgg agaaaggaca gtgggaaaga cactggct cagccaggga      240 atccatttct tccctaaggg ttcagggtag ttgaatgcag atgcacaatc tttcacaccc   300
tcttcctggt gcagcaggtg gctgaatatg ggggaggggt gtcgggtgac agtggagtca   360
gagggcagta cagggcagga tggaaggaca gaaggtatcc cgagaaaggg cagaggaggg   420
tgggt                                                                  425

<210> SEQ ID NO 11
<211> LENGTH: 4560
<212> TYPE: DNA
<213> ORGANISM: C. Elegans

<400> SEQUENCE: 11
attaagaacg aatgagtcga tagaagcact gaaaaatgaa gaaatggcta gttatagtat      60
taattatcgc tggaatacga tgcgacggat tttcggatca agttttccga actctgttca    120
ttggagaagg aaatgcgtgc tatagaactt ttaataaaac gcacgaattc ggttgtcaag    180
gtaaaaattg aatgatttca ataattaca tataaaaaaa tattgcactg ttttttcatt    240
attttcattg aaaattagtg tcaaaatatg tataaatcaa tatttatctg aaaataactg    300
gaaatataga gaaagtgctc caaaatggcc aaaacgttgt caattgccga agacgatact    360
ctataataaa cggcaattgg caactttcgg gctgttttc aacactgttc aatttgtcag     420
atgaaaataa ttttattttc agttaactca agtgattttc tatattgtgg cagtgaaaaa    480
aattcatagg ccattttgta gaattgccga aaataactcc acctctgaat tacatgcatt    540
ttcactagaa aatatcattt acatacattt taatttataa atatccagta tttatttatt    600
ttcttaaact cattttcaag aaaaatattt tcagctaatc gagaaaacga gaatggccta    660
attgttcgaa tcgacaaaca ggaagacttc aaaaatctcg attcttgctg gaattcattt    720
```

```
tatcccaaat attccgggaa atattgggca cttctcccag tcaatttgat tcgtcgtgat      780
acaatttctc aattgaaatc atcgaaatgt cttcctggaa tagtattata taatagtgga      840
gaatctattc atccaggaga tgaatcaaca gcagcttcac atgatgcaga atgtccaaat      900
gctgcaagtg attattatct tcaagataaa aatgaagaat attgtgaaag aaagattaat      960
tctcggggtg ctataacacg agatggatta atgaaaattg attggcggat acaaatggta     1020
tttattgata attcaactga tttggaaatc attgagaaat gttattcaat gttcaataaa     1080
ccaaaagaag atggttcatc tggatatcca tattgtggaa tgagcttccg tttggctaat     1140
atggcggctg gaaattcaga aatttgctat cggcgtggaa aaaacgatgc aaagctgttt     1200
cagatgaata ttgatagcgg gtaggttttt aaattttaag cagttaaaag aggtgaattt     1260
ttgcattatt aaatgcagaa tagaccgtaa atattgcatg atgagatgta tttcatgata     1320
atattcttta agaaaataaa tttgaaaatt tcataggaaa ataaacaaaa ttttgctaaa     1380
cttcatagtt tggcatttct tatctcgttt tttgttaatt tagggggattt tttagtcaat     1440
aattgcaccg attccatgta tctcttttt tcgaatgata ttgtacctat atgccagacg      1500
agctataatt tcctaatttt aaaaaataaa ttgtccaact caatgcctca atagttgaag     1560
ttttccagag atgctcctca actctgtggt gcaatgcaca gtgacaatat atttgcattt     1620
ccaactccaa ttccaacttc tccaacaaat gagacaataa tcacgagcaa atatatgatg     1680
gtaactgctc gaatggacag ttttggaatg attccagaga tttctgttgg cgaagtatcc     1740
gtactaactt caattatttc tgtactcgca gcagctcgat caatgggaac acagatcgaa     1800
aaatggcaga aagcatcgaa tacttcgaat cgtaatgttt tctttgcttt tttcaatggt     1860
gaatcgttgg attatattgg aagtggtgcg gctgcgtatc agatggagta agttggaaaa     1920
tttaatttaa aaaacgttct agaactagta actgatcaaa aaaatttccc tattaacata     1980
aaatggccca aaaattccta aaaatttcaa aatttcaaaa aaaaaaatag ttcgggcaaa     2040
aaacataatt ctagctgaaa cctcaaattt ggcaagcttt tcaggctcgt aacatatttt     2100
tggaagtcgt caatcaaaaa ataattcagt tttattcatt tatgataatt aattaaaatt     2160
ttccaacatt gtttgaaaat tttataatg atatttggtc attttaccat aattggaatg      2220
gttttcaatt attttcccac tcttccttta gagaaaaaat atatttgtct tcagaaatgg     2280
aaagttccca caaatgattc gctctgatcg aacacacatt catccaattc gcccgaatga     2340
gttagattat atactggaag tacaacaaat tggagttgct aaaggacgaa atatattgt      2400
acacgttgat ggagaacgat atcaacagaa taagacacag acagatcgag ttattgatcg     2460
aattgaacga ggtcttcgta gtcatgcttt tgatcttgaa aaaccatctg gaagtggaga     2520
taggtgggtg catcgaaaat agttttttt ttcaagaaca tacagaaaac gaaaagcttt      2580
taaagcatttt tctttaaaaa ttaaaacaat ttgagcatat gtaaactaca attccgagtg     2640
tcgtttttcg aaaaaagtct aaaattaaaa aaaagcttat cgctcactat ttttcgaaaa     2700
taaggtattt ttccttttaat aaaggcaaac gaaaaatctt cagccatgga taggtgaatt     2760
atagaaataa ttttcaaaaa ttttccttt tcagagttcc acccgcaagt tggcactcgt      2820
ttgccaaggc tgatgctcac gttcaatcag ttctccttgc accatatggt aaagaatatg     2880
aatatcaacg agttaattca attttggata aaaatgagtg gacagaagac gaacgagaga     2940
aagcaattca agagattgaa gctgtttcta ctgctattct ggcagcagcc gctgattatg     3000
ttggagttga aactgatgaa gttgttgcaa aagttgataa aaaaattggta tgtattcttt     3060
```

-continued

```
tttttttttaa ttttaaaact ttcagcgaca atttagatgt tttattgttg aatttgaaat    3120
ttgcagtatt tttaaatact taaaacaaaa tccctgatga cgcagcgatt catcgctgta    3180
ttttctaatt gctgaaattg aattccatat atatggaata tttcatatct ttacatataa    3240
acgttttttt ttttcagata accactatat tcgattgtct catcacttcc aatttctggt    3300
tcgactgtga ttttatgcaa aaactcgatg gcggtcgcta ccacaagctg tttaattcct    3360
acggttttaa tcaaaaatca acatatattt caatggaatc ccatactgca ttccctaccg    3420
tactccattg gttaactatt ttcgctttgg gtagtgacaa agaaacattg aatgtgaaaa    3480
gtgaaaagag ctgctcacat cttggtcaat ttcaagcggt gagttttat tttaaacgaa    3540 tatcaaataa ttaaaatagt tttccgccag tttcagatgt atacctacac gtggcaaccg    3600
aatccgtaca ccggaaattt cagttgtctg aaatctgcaa ttgttaaaaa agtaatggtt    3660
tcgccggctg tagattctca acacccgaa gaagaaatga acacgagata ttcaacatgg    3720
atggaatcag tttatattat tgaatctgtg aatttatatt tgatggaaga tgcttcattt    3780
gaatatacaa tgattctgat tgcggttatt tctgctttat tatcaatctt tgcagttggt    3840
tagttttttt ttcaaaaaaa aaattacaaa aataaatcac aagctttcga gctttctcgt    3900
attcgaaaat gaaggagttt cgcattaaag aaaactagat tttgaatcag ttttttctaat    3960 ctttagagaa attatactca catttgatgc ccagaaaagt ttgcgacttt tgagccaaaa    4020
gcacggtgcc aggtctcgac acgaaaaatt tatattaatt gaaaatatgt ttgcgccttt    4080
aaatggtact gtatttcga attctcattg ctggcgattt aaaaaaatgc atttttaaa    4140 tccataaaag ttgagaaaaa tcgatgaaaa attgcacaga aatgagtgca agaaattaca    4200
gtattcttta aaggcgcaca ccttttcgca tttcacaaaa tttcatcgtg tcgataccgg    4260
gtaccgtatt ttggaggcaa aaatcgcaaa atctcgcgtc tggataatat cgtttatcgt    4320
ttattgaagg aagttttaa aaataagaaa aattgacagc tgcgagaaat tatgcataat    4380
ttataaaaca ataaaaattt ttttttttcag gtcgctgttc tgaaacaaca tttatcgttg    4440
acgagggaga accagcagcg gaaggaggag aacctcttta acaaattatt ctcttcaaca    4500
atgtatcata aattgattaa tttatttaat atttatattc gaaaaaatgt tcccattttt    4560
```

<210> SEQ ID NO 12
<211> LENGTH: 721
<212> TYPE: PRT
<213> ORGANISM: C. Elegans

<400> SEQUENCE: 12

```
Met Lys Lys Trp Leu Val Ile Val Leu Ile Ile Ala Gly Ile Arg Cys
 1               5                   10                  15

Asp Gly Phe Ser Asp Gln Val Phe Arg Thr Leu Phe Ile Gly Glu Gly
            20                  25                  30

Asn Ala Cys Tyr Arg Thr Phe Asn Lys Thr His Glu Phe Gly Cys Gln
        35                  40                  45

Ala Asn Arg Glu Asn Glu Asn Gly Leu Ile Val Arg Ile Asp Lys Gln
    50                  55                  60

Glu Asp Phe Lys Asn Leu Asp Ser Cys Trp Asn Ser Phe Tyr Pro Lys
65                  70                  75                  80

Tyr Ser Gly Lys Tyr Trp Ala Leu Leu Pro Val Asn Leu Ile Arg Arg
                85                  90                  95

Asp Thr Ile Ser Gln Leu Lys Ser Ser Lys Cys Leu Ser Gly Ile Val
            100                 105                 110
```

-continued

```
Leu Tyr Asn Ser Gly Glu Ser Ile His Pro Gly Asp Glu Ser Thr Ala
            115                 120                 125

Ala Ser His Asp Ala Glu Cys Pro Asn Ala Ala Ser Asp Tyr Tyr Leu
    130                 135                 140

Gln Asp Lys Asn Glu Glu Tyr Cys Glu Arg Lys Ile Asn Ser Arg Gly
145                 150                 155                 160

Ala Ile Thr Arg Asp Gly Leu Met Lys Ile Asp Trp Arg Ile Gln Met
                165                 170                 175

Val Phe Ile Asp Asn Ser Thr Asp Leu Glu Ile Ile Glu Lys Cys Tyr
            180                 185                 190

Ser Met Phe Asn Lys Pro Lys Glu Asp Gly Ser Ser Gly Tyr Pro Tyr
        195                 200                 205

Cys Gly Met Ser Phe Arg Leu Ala Asn Met Ala Ala Gly Asn Ser Glu
    210                 215                 220

Ile Cys Tyr Arg Arg Gly Lys Asn Asp Ala Lys Leu Phe Gln Met Asn
225                 230                 235                 240

Ile Asp Ser Gly Asp Ala Pro Gln Leu Cys Gly Ala Met His Ser Asp
                245                 250                 255

Asn Ile Phe Ala Phe Pro Thr Pro Ile Pro Thr Ser Pro Thr Asn Glu
            260                 265                 270

Thr Ile Ile Thr Ser Lys Tyr Met Met Val Thr Ala Arg Met Asp Ser
        275                 280                 285

Phe Gly Met Ile Pro Glu Ile Ser Val Gly Glu Val Ser Val Leu Thr
    290                 295                 300

Ser Ile Ile Ser Val Leu Ala Ala Ala Arg Ser Met Gly Thr Gln Ile
305                 310                 315                 320

Glu Lys Trp Gln Lys Ala Ser Asn Thr Ser Asn Arg Asn Val Phe Phe
                325                 330                 335

Ala Phe Phe Asn Gly Glu Ser Leu Asp Tyr Ile Gly Ser Gly Ala Ala
            340                 345                 350

Ala Tyr Gln Met Glu Asn Gly Lys Phe Pro Gln Met Ile Arg Ser Asp
        355                 360                 365

Arg Thr His Ile His Pro Ile Arg Pro Asn Glu Leu Asp Tyr Ile Leu
    370                 375                 380

Glu Val Gln Gln Ile Gly Val Ala Lys Gly Arg Lys Tyr Tyr Val His
385                 390                 395                 400

Val Asp Gly Glu Arg Tyr Gln Gln Asn Lys Thr Gln Thr Asp Arg Val
                405                 410                 415

Ile Asp Arg Ile Glu Arg Gly Leu Arg Ser His Ala Phe Asp Leu Glu
            420                 425                 430

Lys Pro Ser Gly Ser Gly Asp Arg Val Pro Pro Ala Ser Trp His Ser
        435                 440                 445

Phe Ala Lys Ala Asp Ala His Val Gln Ser Val Leu Leu Ala Pro Tyr
    450                 455                 460

Gly Lys Glu Tyr Glu Tyr Gln Arg Val Asn Ser Ile Leu Asp Lys Asn
465                 470                 475                 480

Glu Trp Thr Glu Asp Glu Arg Glu Lys Ala Ile Gln Glu Ile Glu Ala
                485                 490                 495

Val Ser Thr Ala Ile Leu Ala Ala Ala Asp Tyr Val Gly Val Glu
            500                 505                 510

Thr Asp Glu Val Val Ala Lys Val Asp Lys Lys Leu Ile Thr Thr Ile
        515                 520                 525

Phe Asp Cys Leu Ile Thr Ser Asn Phe Trp Phe Asp Cys Asp Phe Met
```

-continued

```
         530                 535                 540
Gln Lys Leu Asp Gly Gly Arg Tyr His Lys Leu Phe Asn Ser Tyr Gly
545                 550                 555                 560

Phe Asn Gln Lys Ser Thr Tyr Ile Ser Met Glu Ser His Thr Ala Phe
                565                 570                 575

Pro Thr Val Leu His Trp Leu Thr Ile Phe Ala Leu Gly Ser Asp Lys
            580                 585                 590

Glu Thr Leu Asn Val Lys Ser Glu Lys Ser Cys Ser His Leu Gly Gln
        595                 600                 605

Phe Gln Ala Met Tyr Thr Tyr Thr Trp Gln Pro Asn Pro Tyr Thr Gly
    610                 615                 620

Asn Phe Ser Cys Leu Lys Ser Ala Ile Val Lys Lys Val Met Val Ser
625                 630                 635                 640

Pro Ala Val Asp Ser Gln Thr Pro Glu Glu Met Asn Thr Arg Tyr
                645                 650                 655

Ser Thr Trp Met Glu Ser Val Tyr Ile Ile Glu Ser Val Asn Leu Tyr
                660                 665                 670

Leu Met Glu Asp Ala Ser Phe Glu Tyr Thr Met Ile Leu Ile Ala Val
            675                 680                 685

Ile Ser Ala Leu Leu Ser Ile Phe Ala Val Gly Arg Cys Ser Glu Thr
        690                 695                 700

Thr Phe Ile Val Asp Glu Gly Glu Pro Ala Ala Glu Gly Gly Glu Pro
705                 710                 715                 720

Leu
```

<210> SEQ ID NO 13
<211> LENGTH: 2949
<212> TYPE: DNA
<213> ORGANISM: human

<400> SEQUENCE: 13

```
tctgcagaat tcggcttgcg cctggaaaca cgaacttccg gtctcttagg ctccgggcca    60
cagagacggt gtcagtggta gcctagagag gccgctaaca gacaggagcc gaacgggggc   120
ttccgctcag cagagaggca agatggctac ggcagggggt ggctctgggg ctgacccggg   180
aagtcggggt ctccttcgcc ttctgtcttt ctgcgtccta ctagcaggtt tgtgcagggg   240
aaactcagtg gagaggaaga tatatatccc cttaaataaa acagctccct gtgttcgcct   300
gctcaacgcc actcatcaga ttggctgcca gtcttcaatt agtggagaca cagggggttat   360
ccacgtagta gagaaagagg aggacctaca gtgggtattg actgatggcc ccaaccccca   420
ttacatggtt ctgctggaga gcaagcattt taccagggat ttaatggaga agctgaaagg   480
gagaaccagc cgaattgctg gtcttgcagt gtccttgacc aagcccagtc ctgcctcagg   540
cttctctcct agtgtacagt gcccaaatga tgggtttggt gtttactcca attcctatgg   600
gccagagttt gctcactgca gagaaataca gtggaattcg ctgggcaatg gtttggctta   660
tgaagacttt agtttcccca tcttttcttct tgaagatgaa aatgaaacca agtcatcaa    720
gcagtgctat caagatcaca acctgagtca gaatggctca gcaccaacct tcccactatg   780
tgccatgcag ctcttttcac acatgcatgc tgtcatcagc actgccacct gcatgcggcg   840
cagctccatc caaagcacct tcagcatcaa cccagaaatc gtctgtgacc ccctgtctga   900
ttacaatgtg tggagcatgc taaagcctat aaatacaact gggacattaa agcctgacga   960
cagggttgtg gttgctgcca cccggctgga tagtcgttcc ttttttctgga atgtggcccc  1020
```

-continued

```
agggctgaa agcgcagtgg cttcctttgt cacccagctg gctgctgctg aagctttgca    1080
aaaggcacct gatgtgacca ccctgccccg caatgtcatg tttgtcttct ttcaagggga    1140
aacttttgac tacattggca gctcgaggat ggtctacgat atggagaagg gcaagtttcc    1200
cgtgcagtta gagaatgttg actcatttgt ggagctggga caggtggcct taagaacttc    1260
attagagctt tggatgcaca cagatcctgt ttctcagaaa aatgagtctg tacggaacca    1320
ggtggaggat ctcctggcca cattggagaa gagtggtgct ggtgtccctg ctgtcatcct    1380
caggaggcca aatcagtccc agcctctccc accatcttcc ctgcagcgat tcttcgagc    1440 tcgaaacatc tctggcgttg ttctggctga ccactctggt gccttccata caaatatta    1500 ccagagtatt tacgacactg ctgagaacat taatgtgagc tatcccgaat ggctgagccc    1560
tgaagaggac ctgaactttg taacagacac tgccaaggcc ctggcagatg tggccacggt    1620
gctgggacgt gctctgtatg agcttgcagg aggaaccaac ttcagcgaca cagttcaggc    1680
tgatccccaa acgttacccc gcctgctcta tgggttcctg attaaagcca caactcatg    1740 gttccagtct atcctcaggc aggacctaag gtcctacttg ggtgacgggc tcttcaaca    1800 ttacatcgct gtctccagcc ccaccaacac cacttatgtt gtacagtatg ccttggcaaa    1860
tttgactggc acagtggtca acctcacccg agagcagtgc caggatccaa gtaaagtccc    1920
aagtgaaaac aaggatctgt atgagtactc atgggtccag ggccctttgc attctaatga    1980
gacggaccga ctcccccggt gtgtgcgttc tactgcacga ttagccaggg ccttgtctcc    2040
tgcctttgaa ctgagtcagt ggagctctac tgaatactct acatggactg agagccgctg    2100
gaaagatatc cgtgcccgga tatttctcat cgccagcaaa gagcttgagt tgatcaccct    2160
gacagtgggc ttcggcatcc tcatcttctc cctcatcgtc acctactgca tcaatgccaa    2220
agctgatgtc cttttcattg ctccccggga gccaggagct gtgtcatact gagsaggacc    2280
scagcttttc ttgccagctc agcagttcac ttcctagagc atctgtccca ctgggacaca    2340
accactaatt tgtcactgga acctccctgg gcctgtctca gattgggatt aacataaaag    2400
agtggaacta tccaaaagag acagggagaa ataaataaat tgcctccctt cctccgctcc    2460
cctttcccat caccccttcc ccatttcctc ttccttctct actcatgcca gattttggga    2520
ttacaaatag aagcttcttg ctcctgttta actccctagt tacccaccct aatttgccct    2580
tcaggaccct tctacttttt ccttcctgcc ctgtacctct ctctgctcct cacccccacc    2640
cctgtaccca gccaccttcc tgactgggaa ggacataaaa ggtttaatgt cagggtcaaa    2700
ctacattgag ccccctgagga cagggcatc tctgggctga gcctactgtc tccttcccac    2760
tgtcctttct ccaggccctc agatggcaca ttagggtggg cgtgctgcgg gtgggtatcc    2820
cacctccagc ccacagtgct cagttgtact ttttattaag ctgtaatatc tatttttgtt    2880
tttgtctttt tcctttattc tttttgtaaa tatatatata atgagtttca ttaaaataga    2940
ttatcccac                                                           2949
```

<210> SEQ ID NO 14
<211> LENGTH: 709
<212> TYPE: PRT
<213> ORGANISM: human

<400> SEQUENCE: 14

```
Met Ala Thr Ala Gly Gly Gly Ser Gly Ala Asp Pro Gly Ser Arg Gly
 1               5                  10                  15

Leu Leu Arg Leu Leu Ser Phe Cys Val Leu Leu Ala Gly Leu Cys Arg
            20                  25                  30
```

-continued

```
Gly Asn Ser Val Glu Arg Lys Ile Tyr Ile Pro Leu Asn Lys Thr Ala
         35                  40                  45
Pro Cys Val Arg Leu Leu Asn Ala Thr His Gln Ile Gly Cys Gln Ser
     50                  55                  60
Ser Ile Ser Gly Asp Thr Gly Val Ile His Val Val Glu Lys Glu Glu
 65                  70                  75                  80
Asp Leu Gln Trp Val Leu Thr Asp Gly Pro Asn Pro Pro Tyr Met Val
                     85                  90                  95
Leu Leu Glu Ser Lys His Phe Thr Arg Asp Leu Met Glu Lys Leu Lys
                100                 105                 110
Gly Arg Thr Ser Arg Ile Ala Gly Leu Ala Val Ser Leu Thr Lys Pro
            115                 120                 125
Ser Pro Ala Ser Gly Phe Ser Pro Ser Val Gln Cys Pro Asn Asp Gly
        130                 135                 140
Phe Gly Val Tyr Ser Asn Ser Tyr Gly Pro Glu Phe Ala His Cys Arg
145                 150                 155                 160
Glu Ile Gln Trp Asn Ser Leu Gly Asn Gly Leu Ala Tyr Glu Asp Phe
                165                 170                 175
Ser Phe Pro Ile Phe Leu Leu Glu Asp Glu Asn Glu Thr Lys Val Ile
                180                 185                 190
Lys Gln Cys Tyr Gln Asp His Asn Leu Ser Gln Asn Gly Ser Ala Pro
            195                 200                 205
Thr Phe Pro Leu Cys Ala Met Gln Leu Phe Ser His Met His Ala Val
        210                 215                 220
Ile Ser Thr Ala Thr Cys Met Arg Arg Ser Ser Ile Gln Ser Thr Phe
225                 230                 235                 240
Ser Ile Asn Pro Glu Ile Val Cys Asp Pro Leu Ser Asp Tyr Asn Val
                245                 250                 255
Trp Ser Met Leu Lys Pro Ile Asn Thr Thr Gly Thr Leu Lys Pro Asp
            260                 265                 270
Asp Arg Val Val Ala Ala Thr Arg Leu Asp Ser Arg Ser Phe Phe
        275                 280                 285
Trp Asn Val Ala Pro Gly Ala Glu Ser Ala Val Ala Ser Phe Val Thr
        290                 295                 300
Gln Leu Ala Ala Ala Glu Ala Leu Gln Lys Ala Pro Asp Val Thr Thr
305                 310                 315                 320
Leu Pro Arg Asn Val Met Phe Val Phe Phe Gln Gly Glu Thr Phe Asp
                325                 330                 335
Tyr Ile Gly Ser Ser Arg Met Val Tyr Asp Met Glu Lys Gly Lys Phe
            340                 345                 350
Pro Val Gln Leu Glu Asn Val Asp Ser Phe Val Glu Leu Gly Gln Val
        355                 360                 365
Ala Leu Arg Thr Ser Leu Glu Leu Trp Met His Thr Asp Pro Val Ser
        370                 375                 380
Gln Lys Asn Glu Ser Val Arg Asn Gln Val Glu Asp Leu Leu Ala Thr
385                 390                 395                 400
Leu Glu Lys Ser Gly Ala Gly Val Pro Ala Val Ile Leu Arg Arg Pro
                405                 410                 415
Asn Gln Ser Gln Pro Leu Pro Pro Ser Leu Gln Arg Phe Leu Arg
            420                 425                 430
Ala Arg Asn Ile Ser Gly Val Val Leu Ala Asp His Ser Gly Ala Phe
        435                 440                 445
```

```
His Asn Lys Tyr Tyr Gln Ser Ile Tyr Asp Thr Ala Glu Asn Ile Asn
    450                 455                 460

Val Ser Tyr Pro Glu Trp Leu Ser Pro Glu Asp Leu Asn Phe Val
465                 470                 475                 480

Thr Asp Thr Ala Lys Ala Leu Ala Asp Val Ala Thr Val Leu Gly Arg
                485                 490                 495

Ala Leu Tyr Glu Leu Ala Gly Gly Thr Asn Phe Ser Asp Thr Val Gln
            500                 505                 510

Ala Asp Pro Gln Thr Val Thr Arg Leu Leu Tyr Gly Phe Leu Ile Lys
        515                 520                 525

Ala Asn Asn Ser Trp Phe Gln Ser Ile Leu Arg Gln Asp Leu Arg Ser
    530                 535                 540

Tyr Leu Gly Asp Gly Pro Leu Gln His Tyr Ile Ala Val Ser Ser Pro
545                 550                 555                 560

Thr Asn Thr Thr Tyr Val Val Gln Tyr Ala Leu Ala Asn Leu Thr Gly
                565                 570                 575

Thr Val Val Asn Leu Thr Arg Glu Gln Cys Gln Asp Pro Ser Lys Val
            580                 585                 590

Pro Ser Glu Asn Lys Asp Leu Tyr Glu Tyr Ser Trp Val Gln Gly Pro
        595                 600                 605

Leu His Ser Asn Glu Thr Asp Arg Leu Pro Arg Cys Val Arg Ser Thr
    610                 615                 620

Ala Arg Leu Ala Arg Ala Leu Ser Pro Ala Phe Glu Leu Ser Gln Trp
625                 630                 635                 640

Ser Ser Thr Glu Tyr Ser Thr Trp Thr Glu Ser Arg Trp Lys Asp Ile
                645                 650                 655

Arg Ala Arg Ile Phe Leu Ile Ala Ser Lys Glu Leu Glu Leu Ile Thr
            660                 665                 670

Leu Thr Val Gly Phe Gly Ile Leu Ile Phe Ser Leu Ile Val Thr Tyr
        675                 680                 685

Cys Ile Asn Ala Lys Ala Asp Val Leu Phe Ile Ala Pro Arg Glu Pro
    690                 695                 700

Gly Ala Val Ser Tyr
705

<210> SEQ ID NO 15
<211> LENGTH: 2250
<212> TYPE: DNA
<213> ORGANISM: mouse

<400> SEQUENCE: 15
cccagcggag aggcaacatg gctacgacta ggggcggctc tgggcctgac ccaggaagtc      60
ggggtcttct tcttctgtct ttttccgtgg tactggcagg attgtgtggg ggaaactcag     120
tggagaggaa aatctacatt cccttaaata aaacagctcc ttgtgtccgc ctgctcaacg     180
ccactcatca gattggctgc cagtcttcaa ttagtgggga tacaggggtt atccacgtag     240
tggagaaaga agaagacctg aagtgggtgt tgaccgatgg ccccaacccc ccttacatgg     300
ttctgctgga gggcaagctc ttcaccagag atgtaatgga gaagctgaag ggaacaacca     360
gtagaatcgc tggtcttgcc gtgactctag ccaagcccaa ctcaacttca agcttctctc     420
ctagtgtgca gtgcccaaat gatgggtttg gtatttactc caactcctac gggccagagt     480
ttgctcactg caagaaaaca ctgtggaata actgggcaa cggcttggct tatgaagact     540
ttagtttccc catctttctt cttgaagatg agaacgaaac caaggtcatc aagcagtgct     600
```

```
atcaagatca aacctgggt cagaatggct ctgcaccaag cttcccattg tgtgctatgc      660
agctcttctc acacatgcac gccgtcatca gcactgccac ctgcatgcgg cgcagcttca      720
tccagagcac cttcagcatc aacccagaaa tcgtctgtga cccttatct gactacaacg      780
tatggagcat gcttaagcct ataaatacat ctgtgggact agaacctgac gtcagggttg      840
tggttgcggc cacacggctg gatagccggt ccttttttctg gaatgtggcc ccaggggctg      900
aaagtgctgt agcctccttt gtcactcagc tggctgcagc tgaagctttg cacaaggcac      960
ctgatgtgac cactctatcc cgaaatgtga tgtttgtctt cttccagggg gaaactttg     1020
actacattgg cagctcacgg atggtctatg atatggagaa cggcaagttt cccgtgcggc     1080
tcgagaacat cgactccttc gtggagctgg acaggtggc cctaagaact tcactagatc     1140
tctggatgca cacagatccc atgtctcaga aaatgagtc tgtgaaaaac caggtggagg     1200
atcttctggc cactctggag aagagcggtg ctggtgtccc tgaagttgtc ctgaggagac     1260
tggcccagtc ccaggccctt ccaccttcat ctctacaacg atttcttcgg gctcgaaaca     1320
tctctggcgt ggtcctggct gaccactctg ctccttcca caatcggtat accagagca      1380
tttatgacac ggctgagaac attaatgtga cctatcctga gtggcagagc ccagaagagg     1440
acctcaactt tgtgacagac actgccaagg cactggcgaa tgtggccaca gtgctggcgc     1500
gtgcactgta tgagcttgca ggaggaacca acttcagcag ctccatccag gctgatcccc     1560
agacagttac acgtctgctc tatgggttcc tggttaaagc taacaactca tggtttcagt     1620
cgatcctgaa acatgaccta aggtcctatt tggatgacag gcctcttcaa cactacatcg     1680
ccgtctccag ccctaccaac acgacttacg ttgtgcagta cgccttggca aacctgactg     1740
gcaaggcgac caacctcacc cgagagcagt gccaggatcc aagtaaagtc ccaaatgaga     1800
gcaaggattt atatgaatac tcgtgggtac aaggcccttg gaattccaac aggacagaga     1860
ggctcccaca gtgtgtgcgc tccacagtgc gactggccag ggccttgtcc cctgcctttg     1920
aactgagtca gtggagctcc acagaatact ctacgtgggc ggagagccgc tggaaagaca     1980
tccaagctcg gatattccta attgccagca aaaagcttga gttcatcacg ctgatcgtgg     2040
gcttcagcat ccttatcttc tctctcatcg tcacctactg catcaatgcc aaagccgacg     2100
tcctttttgt tgctccccga gagccaggag ctgtgtctta ctgaagagga ctctagctct     2160
ccctgcctgc tctgaacttt acttcccaga ccaggtgtcc ggctgggaac aaaccactaa     2220
tttgtcactg gactgtctct gggcctgctt                                      2250
```

<210> SEQ ID NO 16
<211> LENGTH: 708
<212> TYPE: PRT
<213> ORGANISM: mouse

<400> SEQUENCE: 16

Met Ala Thr Thr Arg Gly Gly Ser Gly Pro Asp Pro Gly Ser Arg Gly
1               5                   10                  15

Leu Leu Leu Leu Ser Phe Ser Val Val Leu Ala Gly Leu Cys Gly Gly
            20                  25                  30

Asn Ser Val Glu Arg Lys Ile Tyr Ile Pro Leu Asn Lys Thr Ala Pro
        35                  40                  45

Cys Val Arg Leu Leu Asn Ala Thr His Gln Ile Gly Cys Gln Ser Ser
    50                  55                  60

Ile Ser Gly Asp Thr Gly Val Ile His Val Val Glu Lys Glu Glu Asp
65                  70                  75                  80

-continued

```
Leu Lys Trp Val Leu Thr Asp Gly Pro Asn Pro Pro Tyr Met Val Leu
                 85                  90                  95

Leu Glu Gly Lys Leu Phe Thr Arg Asp Val Met Glu Lys Leu Lys Gly
                100                 105                 110

Thr Thr Ser Arg Ile Ala Gly Leu Ala Val Thr Leu Ala Lys Pro Asn
                115                 120                 125

Ser Thr Ser Ser Phe Ser Pro Ser Val Gln Cys Pro Asn Asp Gly Phe
            130                 135                 140

Gly Ile Tyr Ser Asn Ser Tyr Gly Pro Glu Phe Ala His Cys Lys Lys
145                 150                 155                 160

Thr Leu Trp Asn Glu Leu Gly Asn Gly Leu Ala Tyr Glu Asp Phe Ser
                165                 170                 175

Phe Pro Ile Phe Leu Leu Glu Asp Glu Asn Glu Thr Lys Val Ile Lys
                180                 185                 190

Gln Cys Tyr Gln Asp His Asn Leu Gly Gln Asn Gly Ser Ala Pro Ser
                195                 200                 205

Phe Pro Leu Cys Ala Met Gln Leu Phe Ser His Met His Ala Val Ile
            210                 215                 220

Ser Thr Ala Thr Cys Met Arg Arg Ser Phe Ile Gln Ser Thr Phe Ser
225                 230                 235                 240

Ile Asn Pro Glu Ile Val Cys Asp Pro Leu Ser Asp Tyr Asn Val Trp
                245                 250                 255

Ser Met Leu Lys Pro Ile Asn Thr Ser Val Gly Leu Glu Pro Asp Val
                260                 265                 270

Arg Val Val Ala Ala Thr Arg Leu Asp Ser Arg Ser Phe Phe Trp
                275                 280                 285

Asn Val Ala Pro Gly Ala Glu Ser Ala Val Ala Ser Phe Val Thr Gln
            290                 295                 300

Leu Ala Ala Ala Glu Ala Leu His Lys Ala Pro Asp Val Thr Thr Leu
305                 310                 315                 320

Ser Arg Asn Val Met Phe Val Phe Gln Gly Glu Thr Phe Asp Tyr
                325                 330                 335

Ile Gly Ser Ser Arg Met Val Tyr Asp Met Glu Asn Gly Lys Phe Pro
                340                 345                 350

Val Arg Leu Glu Asn Ile Asp Ser Phe Val Glu Leu Gly Gln Val Ala
                355                 360                 365

Leu Arg Thr Ser Leu Asp Leu Trp Met His Thr Asp Pro Met Ser Gln
                370                 375                 380

Lys Asn Glu Ser Val Lys Asn Gln Val Glu Asp Leu Leu Ala Thr Leu
385                 390                 395                 400

Glu Lys Ser Gly Ala Gly Val Pro Glu Val Val Leu Arg Arg Leu Ala
                405                 410                 415

Gln Ser Gln Ala Leu Pro Pro Ser Ser Leu Gln Arg Phe Leu Arg Ala
                420                 425                 430

Arg Asn Ile Ser Gly Val Val Leu Ala Asp His Ser Gly Ser Phe His
                435                 440                 445

Asn Arg Tyr Tyr Gln Ser Ile Tyr Asp Thr Ala Glu Asn Ile Asn Val
                450                 455                 460

Thr Tyr Pro Glu Trp Gln Ser Pro Glu Glu Asp Leu Asn Phe Val Thr
465                 470                 475                 480

Asp Thr Ala Lys Ala Leu Ala Asn Val Ala Thr Val Leu Ala Arg Ala
                485                 490                 495

Leu Tyr Glu Leu Ala Gly Gly Thr Asn Phe Ser Ser Ser Ile Gln Ala
```

```
                500             505             510
Asp Pro Gln Thr Val Thr Arg Leu Leu Tyr Gly Phe Leu Val Lys Ala
        515                 520                 525
Asn Asn Ser Trp Phe Gln Ser Ile Leu Lys His Asp Leu Arg Ser Tyr
    530                 535                 540
Leu Asp Asp Arg Pro Leu Gln His Tyr Ile Ala Val Ser Ser Pro Thr
545                 550                 555                 560
Asn Thr Thr Tyr Val Val Gln Tyr Ala Leu Ala Asn Leu Thr Gly Lys
                565                 570                 575
Ala Thr Asn Leu Thr Arg Glu Gln Cys Gln Asp Pro Ser Lys Val Pro
            580                 585                 590
Asn Glu Ser Lys Asp Leu Tyr Glu Tyr Ser Trp Val Gln Gly Pro Trp
        595                 600                 605
Asn Ser Asn Arg Thr Glu Arg Leu Pro Gln Cys Val Arg Ser Thr Val
    610                 615                 620
Arg Leu Ala Arg Ala Leu Ser Pro Ala Phe Glu Leu Ser Gln Trp Ser
625                 630                 635                 640
Ser Thr Glu Tyr Ser Thr Trp Ala Glu Ser Arg Trp Lys Asp Ile Gln
                645                 650                 655
Ala Arg Ile Phe Leu Ile Ala Ser Lys Lys Leu Glu Phe Ile Thr Leu
            660                 665                 670
Ile Val Gly Phe Ser Ile Leu Ile Phe Ser Leu Ile Val Thr Tyr Cys
        675                 680                 685
Ile Asn Ala Lys Ala Asp Val Leu Phe Val Ala Pro Arg Glu Pro Gly
    690                 695                 700
Ala Val Ser Tyr
705

<210> SEQ ID NO 17
<211> LENGTH: 2942
<212> TYPE: DNA
<213> ORGANISM: D. melanogaster

<400> SEQUENCE: 17
tctgatatca tcgccactgt gctgggaatt cggcacgagc gcaacactgc aatttctgga      60
cgcgatttcg tgggaatctt cgatggaaat cgtctgaat  gcggcttcca tatggctgtt     120
aatactgtcg tatggagcaa ctattgctca aggagaaaga acccgcgata agatgtacga     180
gcccattgga ggagctagct gtttccgacg gctgaatggc acccatcaga caggctgttc     240
ctcaacctac tccggttccg tgggcgtact acatctaata aacgtcgagg ccgacctgga     300
atttcttctt agcagcccac catctccacc ttacgccccc atgataccac ctcacctgtt     360
cacacgtaac aacctgatgc gcctaaagga agccggacca agaacatttt ctgtggtgct     420
gctgatcaac cgcacgaacc agatgaagca gttctcgcac gaactcaact gcccaatca      480
gtacagcggc ctgaacagca ccagtgagac ctgcgacgcc agcaatccag ccaaaaactg     540
gaatccctgg ggcactggac ttctgcacga ggactttccc tttcctatct attacataqc     600
cgatttggat caggtcacca gctagagaa gtgctttcag gactttaaca accataacta     660
cgagacgcac gcgctgcgta gcttgtgcgc cgtcgaggtc aagtccttta tgtccgccgc     720
tgtcaacacc gaggtctgta tgcgccgcac caacttcatc aataatcttg gaggaagcaa     780
gtactgcgat ccgctcgagg gacggaatgt ttcgccacct tgtaccccg aaagccagca     840
atcggaaaca actttggaga cagtccatac gaatgaaaag ttcatattag taacctgtcg     900
```

```
cctggacacc accaccatgt tcgatggcgt cggtcttgga gccatggact ccctcatggg    960
atttgctgtt ttcactcatg tggcgtatct attaaaacaa ctacttccgc cgcaaagcaa   1020
agaccttcat aatgtcctct ttgtgacttt taatggcgaa tcctatgact acattggttc   1080
tcaaagattt gtatacgaca tggagaaact tcaatttcct actgaatcca caggcacgcc   1140
tccgattgcc tttgacaata ttgacttcat gctggacatc gggacactgg atgacatatc   1200
gaatattaag ctgcatgcgt taaatggaac gactttggct cagcaaattc tagagcggct   1260
aaataactat gcgaagtcgc cacgctatgg ctttaacctg aacattcagt ccgagatgag   1320
cgctcactta ccacctacgt cggcgcaatc atttctgcga cgtgatccaa acttcaatgc   1380
attgattcta aacgctcgtc aacgaacaa gtattatcat tccacatacg atgacgcgga   1440
taacgtggac ttcacctatg cgaacacaag caaggatttc acccagctga cggaagttaa   1500
tgactttaaa agcttgaacc cagattcact gcaaatgaaa gtgcgcaacg tttcctctat   1560
tgtggccatg gccctatatc agacaataac tggaaaggag tacactggca ccaaggtggc   1620
caaccctctg atggcagatg agttcctta ctgtttcctg caatcggcgg actgcccact   1680
ctttaaggcc gcatcttatc cgggcagtca gctcaccaat ttgcctccga tgcgctacat   1740
aagcgtcttg ggtggctctc aagagtcgtc gggctatacg tatagattgc tgggctatct   1800
cttgtcacaa ctgcagccag acattcacag agataactgc accgacttgc cgctgcacta   1860
tttcgccgga ttcaacaata tcggagagtg tcgcctcacc acgcagaact acagtcacgc   1920
cctgagtcca gcttttctta ttgatggcta cgattggagt tccggcatgt attccacttg   1980
gactgaatcc acctggtcac agttcagtgc acgcatcttc ctgcgcccgt ccaatgtgca   2040
ccaggtcaca actctaagcg ttggcatagt ggtgctgata atatccttct gtttggtgta   2100
tataatcagc tcacgatcgg aagtcctctt tgaggatttg ccggcaagca atgccgcatt   2160
atttggttga tgtcacaact gccacagcga cgaaatcatc gcgttcagca gctcattcca   2220
tagatttctg catgcgtaaa ctaaacgtta cttgtaaacc aatcgattaa gaatttctga   2280
ttgtgccctt ttagatcgcc gcggccgaca gcctgttaaa tcttcaaaga atatctgatc   2340
acgtgccgaa gatgattggt tgctgaatat gatctaaaac aaaaaacaga cttaacaaag   2400
acactaaaat gatattctaa ctcgtcttat ttaaaacatt aagcaaacgt ttatttatat   2460
gtatttttgt attttaaagt agtaaattag cttctatcaa ctacgttgta tcatatatag   2520
acatttaacc aattgcgaca aaattctttc cacttgtccg gcccttttg cattgtacat    2580
aggattaacc aacccaattg aacctctgat aatgccaagg aagagatgtc tgtacaaata   2640
ttgacaagaa actgctataa cttataaatc actggaaata tttataccttt ctgcatctat   2700
tgcgatactg aacttaatga tctgaaatca ttacttcata gaagacaaat aattattata   2760
acgactttaa attatatatg tttaataaat tttgataagg tgtaaagcaa tgtcctgtta   2820
tctagttagg ttattttcaa ggcaattatt cacagctctc agattccaac gattgatgta   2880
gtttaatctc aactctttac caaagaagtc catttgtact agtgtaaaag atattttcaa   2940
ta                                                                  2942
```

<210> SEQ ID NO 18
<211> LENGTH: 695
<212> TYPE: PRT
<213> ORGANISM: D. melanogaster

<400> SEQUENCE: 18

Met Glu Met Arg Leu Asn Ala Ala Ser Ile Trp Leu Leu Ile Leu Ser

-continued

```
  1               5                  10                 15
Tyr Gly Ala Thr Ile Ala Gln Gly Glu Arg Thr Arg Asp Lys Met Tyr
                20                 25                 30

Glu Pro Ile Gly Gly Ala Ser Cys Phe Arg Arg Leu Asn Gly Thr His
                35                 40                 45

Gln Thr Gly Cys Ser Ser Thr Tyr Ser Gly Ser Val Gly Val Leu His
                50                 55                 60

Leu Ile Asn Val Glu Ala Asp Leu Glu Phe Leu Ser Ser Pro Pro
65                 70                 75                 80

Ser Pro Pro Tyr Ala Pro Met Ile Pro Pro His Leu Phe Thr Arg Asn
                85                 90                 95

Asn Leu Met Arg Leu Lys Glu Ala Gly Pro Lys Asn Ile Ser Val Val
                100                105                110

Leu Leu Ile Asn Arg Thr Asn Gln Met Lys Gln Phe Ser His Glu Leu
                115                120                125

Asn Cys Pro Asn Gln Tyr Ser Gly Leu Asn Ser Thr Ser Glu Thr Cys
                130                135                140

Asp Ala Ser Asn Pro Ala Lys Asn Trp Asn Pro Trp Gly Thr Gly Leu
145                150                155                160

Leu His Glu Asp Phe Pro Phe Pro Ile Tyr Tyr Ile Ala Asp Leu Asp
                165                170                175

Gln Val Thr Lys Leu Glu Lys Cys Phe Gln Asp Phe Asn Asn His Asn
                180                185                190

Tyr Glu Thr His Ala Leu Arg Ser Leu Cys Ala Val Glu Val Lys Ser
                195                200                205

Phe Met Ser Ala Ala Val Asn Thr Glu Val Cys Met Arg Arg Thr Asn
                210                215                220

Phe Ile Asn Asn Leu Gly Gly Ser Lys Tyr Cys Asp Pro Leu Glu Gly
225                230                235                240

Arg Asn Val Ser Pro Pro Cys Thr Pro Glu Ser Gln Gln Ser Glu Thr
                245                250                255

Thr Leu Glu Thr Val His Thr Asn Glu Lys Phe Ile Leu Val Thr Cys
                260                265                270

Arg Leu Asp Thr Thr Thr Met Phe Asp Gly Val Gly Leu Gly Ala Met
                275                280                285

Asp Ser Leu Met Gly Phe Ala Val Phe Thr His Val Ala Tyr Leu Leu
                290                295                300

Lys Gln Leu Leu Pro Pro Gln Ser Lys Asp Leu His Asn Val Leu Phe
305                310                315                320

Val Thr Phe Asn Gly Glu Ser Tyr Asp Tyr Ile Gly Ser Gln Arg Phe
                325                330                335

Val Tyr Asp Met Glu Lys Leu Gln Phe Pro Thr Glu Ser Thr Gly Thr
                340                345                350

Pro Pro Ile Ala Phe Asp Asn Ile Asp Phe Met Leu Asp Ile Gly Thr
                355                360                365

Leu Asp Asp Ile Ser Asn Ile Lys Leu His Ala Leu Asn Gly Thr Thr
                370                375                380

Leu Ala Gln Gln Ile Leu Glu Arg Leu Asn Asn Tyr Ala Lys Ser Pro
385                390                395                400

Arg Tyr Gly Phe Asn Leu Asn Ile Gln Ser Glu Met Ser Ala His Leu
                405                410                415

Pro Pro Thr Ser Ala Gln Ser Phe Leu Arg Arg Asp Pro Asn Phe Asn
                420                425                430
```

```
Ala Leu Ile Leu Asn Ala Arg Pro Thr Asn Lys Tyr Tyr His Ser Thr
        435                 440                 445

Tyr Asp Asp Ala Asp Asn Val Asp Phe Thr Tyr Ala Asn Thr Ser Lys
    450                 455                 460

Asp Phe Thr Gln Leu Thr Glu Val Asn Asp Phe Lys Ser Leu Asn Pro
465                 470                 475                 480

Asp Ser Leu Gln Met Lys Val Arg Asn Val Ser Ser Ile Val Ala Met
                485                 490                 495

Ala Leu Tyr Gln Thr Ile Thr Gly Lys Glu Tyr Thr Gly Thr Lys Val
            500                 505                 510

Ala Asn Pro Leu Met Ala Asp Glu Phe Leu Tyr Cys Phe Leu Gln Ser
        515                 520                 525

Ala Asp Cys Pro Leu Phe Lys Ala Ala Ser Tyr Pro Gly Ser Gln Leu
        530                 535                 540

Thr Asn Leu Pro Pro Met Arg Tyr Ile Ser Val Leu Gly Gly Ser Gln
545                 550                 555                 560

Glu Ser Ser Gly Tyr Thr Tyr Arg Leu Leu Gly Tyr Leu Leu Ser Gln
                565                 570                 575

Leu Gln Pro Asp Ile His Arg Asp Asn Cys Thr Asp Leu Pro Leu His
            580                 585                 590

Tyr Phe Ala Gly Phe Asn Asn Ile Gly Glu Cys Arg Leu Thr Thr Gln
        595                 600                 605

Asn Tyr Ser His Ala Leu Ser Pro Ala Phe Leu Ile Asp Gly Tyr Asp
    610                 615                 620

Trp Ser Ser Gly Met Tyr Ser Thr Trp Thr Glu Ser Thr Trp Ser Gln
625                 630                 635                 640

Phe Ser Ala Arg Ile Phe Leu Arg Pro Ser Asn Val His Gln Val Thr
            645                 650                 655

Thr Leu Ser Val Gly Ile Val Val Leu Ile Ile Ser Phe Cys Leu Val
                660                 665                 670

Tyr Ile Ile Ser Ser Arg Ser Glu Val Leu Phe Glu Asp Leu Pro Ala
            675                 680                 685

Ser Asn Ala Ala Leu Phe Gly
            690         695

<210> SEQ ID NO 19
<211> LENGTH: 17
<212> TYPE: PRT
<213> ORGANISM: human

<400> SEQUENCE: 19

Ala Arg Leu Ala Arg Ala Leu Ser Pro Ala Phe Glu Leu Ser Gln Trp
1               5                   10                  15

Ser
```

PRESENILIN ASSOCIATED MEMBRANE PROTEIN AND USES THEREOF

This patent application claims the priority of U.S. provisional patent application Nos. 60/127,452, filed Apr. 1, 1999 and No. 60/173,826, filed Dec. 30, 1999, which is incorporated herein by reference.

FIELD OF THE INVENTION

The present invention relates generally to the field of neurological and physiological dysfunctions associated with neuropsychiatric and developmental diseases, especially Alzheimer's Disease. More particularly, the invention is concerned with the identification of proteins associated with neuropsychiatric and developmental diseases, especially Alzheimer's Disease, and relates to methods of diagnosing these diseases, and to methods of screening for candidate compounds which modulate the interaction of a certain protein, specifically Presenilin Associated Membrane Protein ("PAMP"), with presenilin proteins.

BACKGROUND OF THE INVENTION

Alzheimer's Disease (AD) is a degenerative disorder of the human central nervous system characterized by progressive memory impairment and cognitive and intellectual decline during mid to late adult life (Katzman, *N Eng J Med* 1986;314:964–973). The disease is accompanied by a constellation of neuropathologic features principal amongst which are the presence of extracellular amyloid or senile plaques, and neurofibrillary tangles in neurons. The etiology of this disease is complex, although in some families it appears to be inherited as an autosomal dominant trait. Genetic studies have identified three genes associated with the development of AD, namely: (1) β-amyloid precursor protein (βAPP) (Chartier-Harlin et al., *Nature* 1991;353:844–846; Goate et al., *Nature* 1991;349:704–706; Murrell et al., *Science* 1991:254:97–99; Karlinsky et al., *Neurology* 1992;42:1445–1453; Mullan et al., *Nature Genetics* 1992;1:345–347); (2) presenilin-1 (PS1) (Sherrington et al., *Nature* 1995;375:754–760); and (3) presenilin-2 (PS2) (Rogaev et al., *Nature* 1995;376:775–778; Levy-Lehad et al., *Science* 1995; 269:970–973).

Abnormal processing of βAPP with overproduction of amyloid-β is also a feature of other CNS diseases, including inherited and sporadic forms of amyloid angiopathy, which presents with intracerebral bleeding (Levy et al., *Science* 1990;248:1124–1126). Thus, abnormalities of presenilin proteins and PS-interacting proteins may affect these diseases as well.

The presenilin genes (PS1—PS1 and PS2—PS2) encode homologous polytopic transmembrane proteins that are expressed at low levels in intracellular membranes including the nuclear envelope, the endoplasmic reticulum the Golgi apparatus and some as yet uncharacterized intracytoplasmic vesicles in many different cell types including neuronal and non-neuronal cells (Sherrington et al., supra; Rogaev et al., supra, Levy-Lahad et al., supra; Doan et al., *Neuron* 1996;17:1023–1030; Walter et al., *Molec. Medicine* 1996;2:673–691; De Strooper et al., *J. Biol. Chem.* 1997;272:3590–3598; Lehmann et al., *J.Biol.Chem.* 1997;272:12047–12051; Li et al., *Cell* 1997;90:917–927). Structural studies predict that the presenilins contain between six and eight transmembrane (TM) domains organized such that the N-terminus, the C-terminus, and a large hydrophilic loop following the sixth TM domain are located in the cytoplasm or nucleoplasm, while the hydrophilic loop between TM1 and TM2 is located within the lumen of membranous intracellular organelles (Doan et al., 1996; De Strooper et al., 1997; et al., 1997).

Missense mutations in the PS1 and PS2 genes are associated with the inherited forms of early-onset AD (Sherrington et al., *Nature* 1995;375:754–760; Rogaev, et al., *Nature* 1995;376:775–778; Levy-Lahad et al, *Science* 1995;269:970–973). Several lines of evidence have also suggested roles in developmental, apoptotic signalling and in the regulation of proteolytic cleavage of the β-amyloid precursor protein (βAPP) (Levitan et al., *Nature* 1995;377:351–354; Wong et al., *Nature* 1997;387:288–292; Shen et al., *Cell* 1997;89:629–639; Wolozin et al., *Science* 1996;274:1710–1713; De Strooper et al., *Nature* 1998;391:387–390). Nevertheless, it remains unclear just how these putative functions are mediated, or how they relate to the abnormal metabolism of the βAPP associated with PS1 and PS2 mutations (Martin et al., *NeuroReport* 995;7:217–220; Scheuner et al., *Nature Med.* 1996;2:864–870; Citron et al., *Nature Med.* 1997;3:67–72; Duff et al., *Nature* 1996;383:710–713; Borchelt et al., *Neuron* 1996;17:1005–1013).

P1 and PS2 interact specifically with at least two members of the armadillo family proteins; neuronal plakophilin-related armadillo protein (Paffenholtz et al., *Differentiation* 1997; 61: 293–304; Paffenholtz et al., *Exp Cell Res* 1999; 250: 452–464; Zhou et al., *Neuroreport* 1997; 8: 2085–2090) and β-catenin, that are expressed in both embryonic and post-natal tissues. Moreover, the domains of PS1 and PS2 that interact with these proteins have been identified. Mutations in PS1 and PS2 affect the translocation of β-catenin into the nucleus of both native cells and cells transfected with a mutant PS gene. These interactions and effects are described in detail in co-pending commonly assigned U.S. application Ser. No. 09/227,725, filed Jan. 8, 1999, the disclosure of which is incorporated herein by reference.

The identification and cloning of normal as well as mutant PS1 and PS2 genes and gene products are described in detail in co-pending commonly assigned U.S. application Ser. Nos. 08/431,048, filed Apr. 28, 1995; Ser. No. 08/496,841, filed Jun. 28, 1995; Ser. No. 08/509,359, filed Jul. 31, 1995; and Ser. No. 08/592,541, filed Jan. 26, 1996, the disclosures of which are incorporated herein by reference.

There is speculation that onset of AD may be associated with aberrant interactions between mutant presenilin proteins and normal forms of PS-interacting proteins, and these changes may increase or decrease interactions present with normal PS1, or cause interaction with a mutation-specific PS-interacting protein. Such aberrant interactions also may result from normal presenilins binding to mutant forms of the PS-interacting proteins. Therefore, mutations in the PS-interacting proteins may also be implicated in the development of AD.

While the identification of normal and mutant forms of PS proteins has greatly facilitated development of diagnostics and therapeutics, a need exists for new methods and reagents to more accurately and effectively diagnose and treat AD. In addition, further insights into PS proteins and their interaction with other components may lead to new diagnostic and treatment methods for other related CNS diseases.

SUMMARY OF THE INVENTION

Applicants have discovered that PS1 and PS2 interact specifically with a transmembrane protein, herein referred to as "Presenilin Associated Membrane Protein" or "PAMP", which is expressed in multiple tissues (e.g., brain, kidney, lung, etc.). The product of this gene is therefore implicated in the biochemical pathways affected in Alzheimer's Disease, and may also have a role in other dementias, amyloid angiopathies, and developmental disorders such as spina bifida. This gene, therefore, presents a new therapeutic target for the treatment of Alzheimer's Disease and other neurologic diseases. In addition, PAMP nucleic acids, proteins and peptides, antibodies to PAMP, cells transformed with PAMP nucleic acids, and transgenic animals altered with PAMP nucleic acids that possess various utilities, as described herein for the diagnosis, therapy and continued investigation of Alzheimer's Disease and other neurodegenerative disorders. Furthermore, mutant PAMP nucleic acids, proteins, or peptides, cells transfected with vectors comprising mutant PAMP nucleic acids, transgenic animals expressing mutant PAMP or peptides thereof, and their use in studying Alzheimer's Disease and other neurodegenerative disorders, or developing improved diagnostic or therapeutic methods for such disorders, are presented herein.

Thus, the invention provides isolated and purified presenilin associated membrane protein (PAMP), or a functional fragment thereof, as well as nucleic acids encoding a PAMP. Preferred nucleotide and amino acid sequences are provided herein. The invention further provides probes and primers for PAMP genes. Preferred embodiments include sequences of at least 10, 15 or 20 consecutive nucleotides selected from the disclosed sequences.

The invention also provides isolated and purified mutant PAMP, or a functional fragment thereof, as well as nucleic acids encoding a mutant PAMP, and probes and primers for PAMP genes. Preferred nucleotide and amino acid sequences are provided herein.

Using the nucleic acid and amino acid sequences disclosed herein, methods for identifying allelic variants or heterospecfic homologues of a human PAMP and gene are provided. The methods may be practiced using nucleic acid hybridization or amplification techniques, immunochemical techniques, or any other technique known in the art. The allelic variants may include other normal human alleles as well as mutant alleles of PAMP genes which may be causative of Alzheimer's Disease or other CNS diseases. The heterospecific homologues may be from other mammalian species, such as mice, rats, dogs, cats or non-human primates, or may be from invertebrate species, such as *Drosophila melanogaster* or *Caenorhabditis elegans*. Thus, it is another object of the invention to provide nucleic acids that encode allelic or heterospecific variants of the disclosed sequences, as well as the allelic or heterospecific proteins encoded by them.

The invention also provides vectors, and particularly expression vectors (e.g., cos-Tet vector), which include any of the above-described nucleic acids. It is a further object of the invention to provide vectors in which normal or mutant PAMP nucleic acid sequences are operably joined to exogenous regulatory regions to produce altered patterns of expression, or to exogenous coding regions to produce fusion proteins. Conversely, it is another object to provide nucleic acids in which PAMP regulatory regions are operably joined to exogenous coding regions, including standard marker genes, to produce constructs in which the regulation of PAMP genes may be studied and used in assays or therapeutics.

The invention further provides host cells and transgenic animals transformed with any of the above-described nucleic acids of the invention. The host cells may be prokaryotic or eukaryotic cells and, in particular, may be gametes, zygotes, fetal cells, or stem cells useful in producing transgenic animal models. In one embodiment, the transgenic animal contains a transgene encoding a normal or mutant PAMP, which is expressed in neural cells such that expression can be detected, e.g., by detecting PAMP, mRNA, or protein, and more preferably by detecting a neuroprotective or a neurodegenerative phenotype. For example, the animal might manifest one or more symptoms of a neurodegenerative disease. The animal may be a vertebrate or an invertebrate. In a preferred embodiment, the transgenic animal is a mouse, which encodes a human PAMP. The transgenic animal may further comprise a second transgene encoding a normal or mutant PS1, PS2, or βAPP.

In another embodiment, the invention provides an animal containing a nucleic acid that expresses a PAMP or a mutant PAMP at a higher or lower level relative to expression level in a wild-type animal. The animal may be prepared by homologous recombination mediated targeting of endogenous PAMP nucleic acid. In a preferred embodiment, the animal is prepared by translocation of P-elements or chemical mutagenesis.

The invention also provides a reconstituted system for measuring PAMP activity, comprising PAMP, a mutant PAMP, or functional fragments thereof, and a PAMP substrate. The reconstituted system may be a whole cell. Preferably, the whole cell contains a first nucleic acid that expresses said PAMP and a second nucleic acid that expresses the substrate. Preferably, the substrate comprises PS1 protein, PS2 protein, βAPP, or a surrogate synthetic substrate protein such as Notch, which undergoes proteolytic processing events similar to those of βAPP (Haass C and Selkoe D J. Nature 1998; 391: 387–390; De Strooper B, et al., Nature 1999; 398:518–522; Song W, et al., Proc Natl Acad Sci USA 1999; 96: 6959–6963.; Struhl G and Greenwald I, Nature 1999; 398: 522–525; Ye Y, et al., Nature 1999; 398: 525–529.).

The invention provides, in addition, a complex between a PAMP, or a mutant PAMP, and an agent which provides a detectable conformational or functional change in the PAMP upon interaction with a substance being analyzed for activity st a neurodegenerative disease. The complex may further comprise PS1 protein, PS2 protein or βAPP.

The invention also provides a method for detecting a mutation in PAMP associated with Alzheimer's or a related neurological disorder, comprising obtaining a nucleic acid sample from an individual diagnosed with or suspected of having a neurodegenerative disorder, and sequencing a gene encoding PAMP from said sample.

The invention also invention provides a method for diagnosing individuals predisposed to or having a neurodegenerative disorder, comprising obtaining a nucleic acid sample from an individual diagnosed with or suspected of having a neurodegenerative disorder, and sequencing a gene encoding PAMP from said sample.

The invention also provides a method for diagnosing individuals predisposed to or having a neurodegenerative disorder, comprising obtaining cells that contain nucleic acid encoding PAMP, and under non-pathological conditions, transcribe the nucleic acid, and measuring a level of transcriptional activity of the nucleic acid.

The invention further provides a method for diagnosing individuals predisposed to or having a neurodegenerative disorder, comprising obtaining cells from an individual that express nucleic acid encoding PAMP, or isolating PAMP from said individual, and measuring PAMP activity, for example PAMP expression levels. In an alternative embodiment, the activity or abundance of a PAMP substrate may be measured.

The invention also provides a method for identifying putative agents having anti-neurodegenerative activity, comprising administering one or more putative agents to a transgenic animal and detecting a change in PAMP activity.

The invention also provides a method for identifying putative agents having anti-neurodegenerative activity, comprising adding one or more said agents to the reconstituted system described above, and detecting a change in PAMP activity.

The invention also provides a method for identifying putative agents having anti-neurodegenerative activity, comprising adding one or more said agents to the complex described above, and detecting a conformational change in PAMP.

The invention also provides a method for identifying proteins that interact with PAMP, comprising contacting said substance to the reconstituted system discussed above, and detecting a change in PAMP activity.

Further the invention provides for a method for identifying substances that modulate PAMP activity, comprising contacting a sample containing one or more substances with PAMP, or a PAMP mutant, or functional fragments thereof, and a PAMP substrate, measuring PAMP activity, and determining whether a change in PAMP activity occurs. In a preferred embodiment, the substance is a PAMP inhibitor. In another preferred embodiment, the substance stimulates PAMP activity.

These and other aspects of the invention are further elaborated in the Detailed Description of the Invention and Examples, infra.

DESCRIPTION OF THE DRAWINGS

FIGS. 1A and 1B. Predicted amino acid sequences for human (SEQ ID NO:14), mouse (SEQ ID NO:16), *D.melanogaster* (SEQ ID NO:18) and *C.elegans* (SEQ ID NO:12) orthologues. Residues not conserved in non-human PAMP are blank, conserved residues are aligned, similar residues are denoted by "+".

DETAILED DESCRIPTION OF THE INVENTION

While PS1 and PS2 have been implicated in proper processing of βAPP, and mutations in these proteins have been associated with Alzheimer's Disease, further understanding of the development and progression of this disease, as well as other neurodegenerative diseases, requires a more complete understanding of the functions of the presenilins and other proteins with which they interact. The present invention advantageously identifies such a protein.

PAMP

The invention is based, in part, on the discovery of a novel Type I transmembrane protein that interacts with PS1 and PS2, and with the α- and β-secretase derived fragments of βAPP. The protein has been termed "Presenilin Associated Membrane Protein" (PAMP). As referred to herein, "PAMP" means a native or mutant full-length protein, or fragments thereof, that interacts with the PAMP-interacting domain of a presenilin protein. PAMP is also known under the name "Nicastrin". Human, murine, *D. melanogaster* and *C. elegans* orthologues are provided.

Experimental data indicates that PAMP, PS1, and PS2 exist in the same high molecular weight protein complex, and PAMP and PS1 are both co-localized to intracellular membranes in the endoplasmic reticulum and Golgi apparatus. Abolition of functional expression of a *C. elegans* homologue of this protein leads to the development of Notch-like developmental defects. This shows that PAMP is also intimately involved in the processing of not only βAPP, but also other molecules, such as Notch and its homologues. From expressed sequence tags (EST) databases, it is apparent that, like PS1 and PS2, PAMP is expressed in multiple tissues.

Various structural features characterize PAMP (GenBank; Accession No. Q92542; SEQ ID NO: 14). The nucleotide sequence (SEQ ID NO: 13) of human PAMP predicts that the gene encodes a Type I transmembrane protein of 709 amino acids (SEQ ID NO:14), the protein having a short hydrophilic C-terminus (~20 residues), a hydrophobic transmembrane domain (15–20 residues), and a longer N-terminal hydrophilic domain which contains several potentially functional sequence motifs as listed below in Table 1. The PAMP sequence also contains a Trp-Asp (WD) repeat (residue 226), at least one "DTG" motif (residues 91–93) present in eukaryotic aspartyl proteases, as well as several "DTA/DTAE" motifs (residues 480–482, 504–506) present in viral aspartyl proteases. There are also four conserved cysteine residues in the N-terminal hydrophilic domain (Cys195, Cys213, Cys230, and Cys248 in human PAMP) having a periodocity of 1617 residues, which may form a functional domain (e.g., a metal binding domain or disulfide bridge for tertiary structure stabilization). Subdomains of PAMP have weak homologies to a variety of peptidases. For example, residues 322–343, 361–405, and 451–466 have 46% (p=0.03) similarity to another hypothetical protein; *C. elegans* aminopeptidase hydrolase precursor signal antigen transmembrane receptor zinc glycoprotein (SWISS-PROT; World Wide Web (www) expasy.ch/sprot; Accession No. Q93332).

TABLE 1

| Potential functional sequence motifs in PAMP (SEQ ID NO:14). | |
|---|---|
| Potential function | PAMP Residue |
| N-asparaginyl glycosylation | 44, 101, 290, 492, 698, 964, 1353, 1772, 2209, 2675, 3183, 3715, 4279, 4854, 5436, and 6050. |
| Glycosaminoglycan attachment | 403 |
| Myristolation | 4, 37, 102, 226, 376, 548, 757, 1055, 1497, 1947, 2455, and 3035. |
| Phosphorylation sites for cAMP- and cGMP-dependent protein kinase | 231 |
| Phosphorylation sites for protein kinase C | 114, 383, 724, 1109, 1499, 1983, 2598, and 3223 |
| Phosphorylation sites for casein kinase II | 7, 289, 652, 1026, 1483, 1951, 2425, 3068, and 3717 |

The invention is further based on the identification of conserved functional domains, based on comparison and evaluation of the predicted amino acid sequences of human (SEQ ID NO: 14), murine (SEQ ID NO: 16). *D. melanogaster* (SEQ ID NO: 18), and *C. elegans* (SEQ ID NO: 12) orthologues of PAMP. "PAMP" can be characterized by the presence of conserved structural features, relative to orthologues from *D. melanogaster* and *C. elegans*. Nucleotide sequences encoding homologous hypothetical proteins exist in mice multiple EST, and *C. elegans* (GenBank; World Wide Web (www) ncbi.nlm.nih.gov; Accession No. Z75714;

37% similarity, p=8.7e$^{-26}$) (Wilson et al., *Nature* 1994; 368: 32–38). These hypothetical murine and nematode proteins have a similar topology and contain similar functional motifs to human PAMP. The existence of such homology predicts that similar proteins will be detected in other species including Xenopus, and Zebra fish, to mention a few such possibilities. By comparing the predicted amino acid sequences of human (SEQ ID NO: 14), murine (SEQ ID NO: 16), *D. melanogaster* (SEQ ID NO: 18), and *C. elegans* (SEQ ID NO: 12) PAMP proteins, we have deduced a series of conserved functional domains. One domain has chemical similarities to cyclic nucleotide binding domains of other proteins, and may have some regulatory role on a potential complex formed between PS1:PAMP and the C-terminal fragment of βAPP, derived either from a- or b-secretase. These putative functional domains are sites for therapeutic target development by deploying drugs which might interact with these sites to modulate βAPP processing via this complex.

The term "PAMP" also refers to functionally active fragments of the protein. Such fragments include, but are not limited to, peptides that contain an epitope, e.g., as determined by conventional algorithms such as hydrophilicity/hydrophobicity analysis for antibody epitopes, and amphipathicity or consensus algorithms for T cell epitopes (Spouge, et al., J. Immunol, 138:2204, 1987; Margalit, et al., J. Immunol., 138:2213, 1987; Rothbard, Ann. Inst. Pateur., 137E:518, 1986; Rothbard and Taylor, EMBO J., 7:93, 1988). More preferably, a functionally active fragment of PAMP is a conserved domain, relative to the *D. melanogaster* and *C. elegans* orthologues. A specific functionally active fragment of PAMP is a fragment that interacts with PS1 or PS2, or both.

PAMP also encompasses naturally occurring variants, including other mammalian PAMPs (readily identified, as shown herein for murine PAMP, based on the presence of the structural features set forth above), allelic variants of PAMP from other human sources (including variants containing polymorphisms that are predictive of disease propensity or of response to pharmacological agents), and mutant forms of PAMP or PAMP genes that are associated with neurological diseases and disorders (such as spina bifida), particularly neurodegenerative diseases (such as AD). Also included are artificial PAMP mutants created by standard techniques such as site directed mutagenesis or chemical synthesis.

A PAMP "substrate" may be a polypeptide or protein, or any other type of compound, with which PAMP interacts physiologically. Examples of PAMP substrates include PS1, PS2, and βAPP. Furthermore, A PAMP "ligand" may be a polypeptide, protein, lipid, carbohydrate, vitamin, mineral, amino acid, or any other type of compound which binds to PAMP Hypothetically, PAMP may function as a receptor which modulates PS1/PS2/βAPP processing in response to signal (ligand) dependent interactions with PAMP.

Definitions

In accordance with the present invention there may be employed conventional molecular biology, microbiology, and recombinant DNA techniques within the skill of the art. Such techniques are explained filly in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

If appearing herein, the following terms shall have the definitions set out below.

The use of italics (e.g., *PAMP*) indicates a nucleic acid molecule (cDNA, mRNA, gene, etc.); normal text (e.g., PAMP) indicates the polypeptide or protein.

In a specific embodiment, the term "about" or "approximately" means within 20%, preferably within 10%, and more preferably within 5% of a given value or range. Alternatively, particularly in biological systems which are often responsive to order of magnitude changes, the term about means within an order of magnitude of a given value, preferably within a multiple of about 5-fold, and more preferably within a factor of about 2-fold of a given value.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell.

As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or functional assays, as described infra. A host cell has been "transfected" by exogenous or heterologous DNA when such DNA has been introduced inside the cell. A cell has been "transformed" by exongenous or heterologous DNA when the transfected DNA is expressed and effects a function or phenotype on the cell in which it is expressed. The term "expression system" means a host cell transformed by a compatible expression vector and cultured under suitable conditions e.g. for the expression of a protein coded for by foreign DNA carried by the vector and introduced to the host cell.

Proteins and polypeptides can be made in the host cell by expression of recombinant DNA. As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell, e.g., the naturally occurring form (or forms) of the amino acid-based polymer.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The coding sequences herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the it naturally occurring nucleotides with an analog, and internucleotide modifications.

The term "gene", also called a "structural gene" means a DNA sequence that codes for or corresponds to a particular sequence of ribonucleic acids or amino acids which comprise all or part of one or more proteins, and may or may not include regulatory DNA sequences, such as promoter sequences, which determine for example the conditions under which the gene is expressed.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

A coding sequence is "under the control" or "operatively associated with" of transcriptional and translational control sequences in a cell when RNA polymerase transcribes the coding sequence into mRNA, which then may be trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned", "foreign", or "heterologous" gene or sequence, and may include regulatory or control sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." Recombinant cloning vectors will often include one or more replication systems for cloning or expression, one or more markers for selection in the host, e.g. antibiotic resistance, and one or more expression cassettes.

A "knockout mammal" is a mammal (e.g., mouse) that contains within its genome a specific gene that has been inactivated by the method of gene targeting (see, e.g., U.S. Pat. No. 5,777,195 and U.S. Pat. No. 5,616,491). A knockout mammal includes both a heterozygote knockout (i.e., one defective allele and one wild-type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 9:2623–34, 1995) describes PPCA knock-out mice. Knockout mice can be used to study defects in neurological development or neurodegenerative diseases. Disease phenotypes that develop can provide a platform for further drug discovery.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

Generally, for homologous recombination, the DNA will be at least about 1 kilobase (kb) in length and preferably 3–4 kb in length, thereby providing sufficient complementary sequence for recombination when the knockout construct is introduced into the genomic DNA of the ES cell.

A "knock-in" mammal is a mammal in which an endogenous gene is substituted with a heterologous gene or a modified variant of the endogenous gene (Roemer et al., New Biol. 3:331, 1991). Preferably, the heterologous gene is "knocked-in" to a locus of interest, for example into a gene that is the subject of evaluation of expression or function, thereby linking the heterologous gene expression to transcription from the appropriate promoter (in which case the gene may be a reporter gene; see Elefanty et al., Proc Natl Acad Sci USA 95:11897,1998). This can be achieved by homologous recombination, transposon (Westphal and Leder, Curr Biol 7:530, 1997), using mutant recombination sites (Araki et al., Nucleic Acids Res 25:868, 1997) or PCR (Zhang and Henderson, Biotechniques 25:784, 1998).

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, some progeny of the cell will no longer express the gene, or will express it at a decreased level, as the DNA is now disrupted by the antibiotic resistance gene.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an gene is heterologous to the recombinant vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST (Altschul S F, et al., J Mol Biol 1990; 215: 403–410) or FASTA algorithms, preferably at least 75%, most preferably at least 85%, and even more preferably at least 90%, and which has the same or substantially similar properties or functions as the native or parent protein or enzyme to which it is compared.

An "ortholog" to a protein means a corresponding protein from another species. Orthologous proteins typically have similar functions in different species, and can also be substantially homologous.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs. Motif analysis can be performed using, for example, the program BLOCKS (www.blocks.fhcrc.org).

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, *Version* 7, Madison, Wis.) pileup program, ProteinPredict (dodo.cmpc.columbia.edu/predictprotein), or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used. Moderate stringency hybridization conditions correspond to a higher $T_m$ and high stringency hybridization conditions correspond to the highest $T_m$. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

The present invention provides antisense nucleic acids (including ribozymes), which may be used to inhibit expression of PAMP, e.g., to disrupt a cellular process (such disruption can be used in an animal model or therapeutically). An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, e.g., for cloning full length or a fragment of a protein or polypeptide. In a further embodiment, an oligonucleotide of the invention can form a triple helix with a nucleic acid (genomic DNA or mRNA) encoding a protein or polypeptide. Generally, oligonucleotides are prepared synthetically, preferably on a nucleic acid synthesizer. Accordingly, oligonucleotides can be prepared with non-naturally occurring phosphoester analog bonds, such as thioester bonds, etc. Furthermore, the oligonucleotides herein may also be modified with a label capable of providing a detectable signal, either directly or indirectly. Exemplary labels include radioisotopes, fluorescent molecules, biotin, and the like.

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. No. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH $SCH_3$, F, OCN, $O(CH_2)_n NH_2$ or $O(CH_2)_n CH_3$ where n is from 1 to about 10, $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Presenilin Interacting Proteins

Mutant PS1 and PS2 genes, and their corresponding amino acid sequences are described in Applicants' co-pending U.S. application Ser. No. 08/888,077, filed Jul. 3, 1997, and incorporated herein by reference. Examples of PS1 mutations include I143T, M146L, L171P, F177S, A260V, C263R, P264L, P267S, E280A, E280G, A285V, L286V, Δ291–319, L322V, G384A, L392V, C410Y and 1439V. Examples of PS2 mutations include N141I, M239V and I420T.

The methods of the present invention are not limited to mutant presenilins wherein the PAMP-interacting domain is mutated relative to the wild-type protein. For example, Applicants have observed that mutations in PS1 (e.g., M146L) outside of the interacting domain (loop) also affect β-catenin translocation. These mutations probably disturb the presenilin armadillo interactions by altering the function of a high MW complex which contains, e.g., the presenilin and armadillo proteins, as described in Yu et al., 1998, *J. Biol. Chem.* 273:16460–16475. Moreover, a comparison of the human PS1 (hPS1) and PS2 (hPS2) sequences reveals that these pathogenic mutations are in regions of the PS1 protein which are conserved in the PS2 protein. Therefore, corresponding mutations in corresponding regions of PS2 may also be expected to be pathogenic and are useful in the methods described herein.

Proteins that interact with the presenilins, i.e., PS-interacting proteins, include PAMP, the S5a subunit of the 26S proteasome (GenBank; Accession No. U51007), Rab11 (GenBank; Accession Nos. X56740 and X53143), retinoid X receptor B, also known as nuclear receptor co-regulator or MHC (GenBank Accession Nos. M84820, and X63522), GT24 (GenBank Accession No. U.S.81004), β-catenin (Zhou et al., 1997, *Neuro. Report* (Fast Track) 8:1 025–1029 and Yu et al., supra) as well as armadillo proteins. These and other PS1 binding proteins are described in Applicants' copending commonly assigned U.S. application Ser. No. 08/888,077, filed Jul. 3, 1997, as well as U.S. application Ser. No. 08/592,541, filed Jan. 26, 1996, the disclosures of which are incorporated herein by reference.

PAMP Mutants

PAMP mutants may cause biochemical changes similar to those affecting the onset or progression of Alzheimer Disease. Therefore, artificial PAMP mutations can potentially be used to generate cellular and other model systems to design treatments and preventions for Alzheimer Disease related disorders. Such mutations may also be used for evaluating whether PAMP is involved in the pathogenesis of AD. Since the amyloid-β (Aβ) inducing mutations are found in amino acid residues of a soluble (non-membrane spanning) domain of PAMP, analysis of the normal structure of this domain and the effects of these and other nearby mutations on the structure of this domain (and the other domains of PAMP) provide information for the design of specific molecular therapeutics.

In general, modifications of the sequences encoding the polypeptides described herein may be readily accomplished by standard techniques such as chemical syntheses and site-directed mutagenesis. See Gillman et al., 1979, *Gene* 8:81–97; Roberts et al., 1987, *Nature* 328:731–734; and Innis (ed.), 1990, *PCR Protocols: A Guide to Methods and Applications*, Academic Press, New York. Most modifications are evaluated by routine screening via an assay designed to select for the desired property.

Antibodies to PAMP

According to the invention, PAMP polypeptides produced recombinantly or by chemical synthesis, and fragments or other derivatives or analogs thereof including fission proteins and PAMP mutants, may be used as an immunogen to generate antibodies that recognize the PAMP polypeptide. Such antibodies include but are not limited to polyclonal, monoclonal, chimeric, single chain, Fab fragments, and an Fab expression library. Such an antibody is preferably specific for human PAMP, PAMP originating from other species, or for post-translationally modified (e.g. phosphorylated, glycosylated) PAMP.

Various procedures known in the art may be used for the production of polyclonal antibodies to PAMP polypeptide or derivative or analog thereof. For the production of antibody, various host animals can be immunized by injection with the PAMP polypeptide, or a derivative (e.g., fragment or fusion protein) thereof, including but not limited to rabbits, mice, rats, sheep, goats, etc. In one embodiment, the PAMP polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Antisera may be collected at a chosen time point after immunization, and purified as desired.

For preparation of monoclonal antibodies directed toward the PAMP polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). Production of human antibodies by CDR grafting is described in U.S. Pat. Nos. 5,585,089, 5,693,761, and 5,693,762 to Queen et al., and also in U.S. Pat. No. 5,225,539 to Winter and International Patent Application PCT/WO91/09967 by Adau et al. In an additional embodiment of the invention, monoclonal antibodies can be produced in germ-free animals (International Patent Publication No. WO 89/12690, published 28 Dec. 1989). In fact, according to the invention, techniques developed for the production of "chimeric antibodies" (Morrison et al., J. Bacteriol. 159:870, 1984); Neuberger et al., Nature 312:604–608, 1984; Takeda et al., Nature 314:452–454, 1985) by splicing the genes from a mouse antibody molecule specific for an PAMP polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. No. 4,946,778) can be adapted to produce PAMP polypeptide-specific single chain antibodies. An additional embodiment of the invention utilizes the techniques described for the construction of Fab expression libraries (Huse et al., Science 246:1275–1281, 1989) to allow rapid and easy identification of monoclonal Fab fragments with the desired specificity for an PAMP polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an PAMP polypeptide, one may assay generated hybridomas for a product which binds to an PAMP polypeptide fragment containing such epitope. For selection of an antibody specific to an PAMP polypeptide from a particular species of animal, one can select on the basis of positive binding with PAMP polypeptide expressed by or isolated from cells of that species of animal.

The foregoing antibodies can be used in methods known in the art relating to the localization and activity of the PAMP polypeptide, e.g., for Western blotting, imaging PAMP polypeptide in situ, measuring levels thereof in appropriate physiological samples, etc. using any of the detection techniques mentioned above or known in the art. Such antibodies can be used to identify proteins that interact with PAMP, and to detect conformational or structural changes in PAMP.

In a specific embodiment, antibodies that agonize or antagonize the activity of PAMP polypeptide can be generated. They can also be used to regulate or inhibit PAMP activity intracellular, i.e., the invention contemplates an intracellular antibody (intrabody), e.g., single chain Fv antibodies(see generally, Chen, Mol. Med. Today, 3:160–167, 1997; Spitz et al., Anticancer Res., 16:3415–3422, 1996; Indolfi et al., Nat. Med., 2:634–635, 1996; Kijima et al., Pharmacol. Ther., 68:247–267, 1995).

PAMP Diagnostic Assays

The nucleotide sequence and the protein sequence and the putative biological activity of PAMP or PAMP mutants can all be used for the purposes of diagnosis of individuals who are at-risk for, or who actually have, a variety of neurodegenerative diseases (including Alzheimer's disease, Lewy body variant, Parkinson's disease-dementia complex, amyotrophic lateral sclerosis etc.), neuropsychiatric diseases (schizophrenia, depression, mild cognitive impairment, benign senescent forgetfulness, age-associated memory loss, etc.), developmental disorders associated with defects in intracellular signal transduction mediated by factors such as Notch, Delta, Wingless, etc., and neoplasms (e.g., bowel cancer, etc.) associated with abnormalities of PS1/PAMP/PS2 mediated regulation of cell death pathways. These diagnostic entities can be used by searching for alterations in: the nucleotide sequence of PAMP; in the transcriptional activity of PAMP; in the protein level as monitored by immunological means (e.g., ELISA and Western blots); in the amino acid sequence (as ascertained by Western blotting, amino acid sequence analysis, mass spectroscopy); and/or in the biological activity of the PAMP protein as measured by either in viva methods (e.g., monitoring βAPP processing and the production of amyloid-β peptide (Aβ), or other suitable protein substrates for PAMP including Notch, etc.), or by in vitro assays (using either whole cell or cell-free assays to measure processing of suitable substrates including βAPP or parts thereof, and other proteins such as Notch). Any of these assays can also be performed in a transgenic animal model as well, e.g., to measure the effect of a drug or a mutation or overexpression of a different gene in vivo.

PAMP Screening Assays

Identification and isolation of PAMP provides for development of screening assays, particularly for high throughput screening of molecules that up- or down-regulate the activity of PAMP, e.g., by permitting expression of PAMP in quantities greater than can be isolated from natural sources, or in indicator cells that are specially engineered to indicate the activity of PAMP expressed after transfection or transformation of the cells. Any screening technique known in the art can be used to screen for PAMP agonists or antagonists. The present invention contemplates screens for small molecule ligands or ligand analogs and mimics, as well as screens for natural ligands that bind to and agonize or antagonize the activity of PAMP in vivo. For example, natural products libraries can be screened using assays of the invention for molecules that agonize or antagonize PAMP activity.

Another approach uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th Int. Congress of Biochemistry, Volume 5, Abstract FR:013, 1988; Furka, Int J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publ. No. WO 92/00252; Kocis et al., International Patent Publ. No. WO 9428028) and the like can be used to screen for PAMP ligands according to the present invention.

Knowledge of the primary sequence of the protein, and the similarity of that sequence with proteins of known function, can provide an initial clue as to the inhibitors or antagonists of the protein. As noted above, identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

The PAMP protein sequence (including parts thereof) can be used to deduce the structural organization and topology of PAMP through the use of a variety of techniques including CD spectroscopy, nuclear magnetic resonance (NMR) spectroscopy, X-ray crystallography, and molecular modeling. Sequences for PAMP or PAMP mutants can also be used to identify proteins which interact with PAMP either in concert with PS1 and PS2, or independently, using a variety of methods including co-immunoprecipitation, yeast two hybrid interaction trap assays, yeast three hybrid interaction trap assays, chemical cross-linking and co-precipitation studies, etc. These and other methods are described more fully in co-pending and commonly assigned U.S. application Ser. No. 08/888,077, filed Jul. 3, 1997, and 09/227,725, filed Jan. 8, 1999, both of which are incorporated herein by reference. Identification of these interacting partners will then lead to their use to further delineate the biochemical pathways leading to the above-mentioned diseases.

Finally, the structural analysis of PAMP, when combined with structural analysis of PS1 and PS2, and other proteins which interact with PAMP or PAMP mutants, will identify the structural domains that mediate interactions between these molecules and which also confer biological activity on PAMP (or PAMP and these other molecules). These structural domains, and other functional domains, which can modulate the activity of these structural domains, can all be modified through a variety of means, including but not limited to site-directed mutagenesis, in order to either augment or reduce the biological activity. The structure and topology of these domains can all be used as a basis for the rational design of pharmaceuticals (small molecule conventional drugs or novel carbohydrate, lipid, DNA/RNA or protein-based high molecular weight biological compounds) to modulate (increase or decrease) the activity of PAMP and/or the PAMP PS1/PS2 complex, and/or the activity of the PAMP/other protein complexes. For example, using structural prediction calculations, possibly in conjunction with spectroscopic data like nuclear magnetic resonance, circular dichroism, and other physical-chemical structural data, or crystallographic data, or both, one can generate molecular models for the structure of PAMP. These models, in turn, are important for rational drug design. Drug candidates generated using a rational drug design program can then be applied for the treatment and/or prevention of the above-mentioned diseases, and can be administered through a variety of means including: as conventional small molecules through enteral or parenteral routes; via inclusion in liposome vehicles; through infusion in pumps inserted into various organs (e.g., via Omaya pumps inserted into the cerebral ventricles); via the transplantation of genetically-modified cells expressing recombinant genes; or via the use of biological vectors (e.g., retrovirus, adenovirus, adeno-associated virus, Lentivirus, or herpes simplex virus-based vectors) which allow targeted expression of appropriately modified gene products in selected cell types. It should be noted that the recombinant proteins described above may be the wild-type PAMP, a genetically-modified PAMP, a wild-type PS1/PS2, a genetically-modified PS1/PS2, or a specially-designed protein or peptide which is designed to interact with either the functional domains of PAMP (or the PAMP/PS1/PS2/other protein complex) or to interact with the domains which modulate the activity of the functional domains of PAMP.

PAMP In Vitro and In Vivo Models

The PAMP nucleotide sequence can be used to make cell-free systems, transfected cell lines, and animal models (invertebrate or vertebrate) of the neurodegenerative and other diseases outlined above. These animal and cell models may involve over-expression of all or part of PAMP or PAMP mutants, e.g., as mini-gene cDNA transgene constructs under the regulation of suitable promoter elements carried in vectors such as cos-Tet for transgenic mice and pcDNA (Invitrogen, California) in transfected cell lines. Animal and cellular models can also be generated by via homologous recombination mediated targeting of the endogenous gene to create artificially mutant sequences (knock-in gene targeting); or loss of function mutations (knock-out gene targeting); by translocation of P-elements; and by chemical mutagenesis. Animal, cellular and cell-free model systems can be used for a variety of purposes including the discovery of diagnostics and therapeutics for this disease.

Included within the scope of this invention is a mammal in which two or more genes have been knocked out or knocked in, or both. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. No. 4,959,317 and U.S. Pat. No. 5,801,030).

Transgenic mammals can be prepared for evaluating the molecular mechanisms of PAMP, and particularly human PAMP/PS1 or PAMP/PS2 function. Such mammals provide excellent models for screening or testing drug candidates. It is possible to evaluate compounds or diseases on "knockout" animals, e.g., to identify a compound that can compensate for a defect in PAMP activity. Alternatively, PAMP (or mutant PAMP), alone or in combination with βAPP, PS1, and/or PS2, (double or triple transgenics) "knock-in" mammals can be prepared for evaluating the molecular biology of this system in greater detail than is possible with human subjects. Both technologies permit manipulation of single units of genetic information in their natural position in a cell genome and to examine the results of that manipulation in the background of a terminally differentiated organism. These animals can be evaluated for levels of mRNA or protein expression, processing of βAPP, or development of a condition indicative of inappropriate gene expression, e.g., Notch phenotype or another phenotype as set forth above, or neurodegeneration, including cognitive deficits, learning or memory deficits, or neuromuscular deficits.

Various transgenic animal systems have been developed. Mice, rats, hamsters, and other rodents are popular, particularly for drug testing, because large numbers of transgenic animals can be bred economically and rapidly. Larger animals, including sheep, goats, pigs, and cows, have been made transgenic as well. Transgenic *D.melanogaster* and *C.elegans* can also be made and, using known genetic methods, may offer the ability to identify upstream and downstream modifiers of a PAMP phenotype. Transgenic animals can also be prepared by introducing the transgene on a vector; such animals, which are not modified in the germ line and are only transiently transgenic, naturally cannot pass along the genetic information to their progeny.

In another series of embodiments, transgenic animals are created in which (i) a human PAMP, or a mutant human PAMP, is stably inserted into the genome of the transgenic animal; and/or (ii) the endogenous PAMP genes are inactivated and replaced with their human counterparts. See, e.g., Coffman, Semin. Nephrol. 17:404, 1997; Esther et al., Lab. Invest. 74:953, 1996; Murakami et al., Blood Press. Suppl. 2:36, 1996. Such animals can be treated with candidate compounds and monitored for the effects of such drugs on PAMP cavity.

PAMP Gene Therapy

As discussed above, abnormalities in PAMP expression and/or interactions with PS1/PS2/βAPP are associated with severe neurological deficits. Thus, the present invention provides for treatment of such deficits either with a drug discovered using a screening assay or transgenic animal model, or both, as set forth above, or by replacing a defective PAMP gene with a functional gene by gene therapy.

A gene encoding PAMP, a PAMP mutant, or alternatively a negative regulator of PAMP such as an antisense nucleic acid, intracellular antibody (intrabody), or dominant negative PAMP (which may be truncated), can be introduced in vivo, ex vivo, or in vitro using a viral or a non-viral vector, e.g., as discussed above. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin 12 (IL-12), interferon-γ (IFNγ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Herpes virus vectors. Because herpes virus is trophic for cells of the nervous system (neural cells), it is an attractive vector for delivery of function PAMP genes. Various defective (non-replicating, and thus non-infectious) herpes virus vectors have been described, such as a defective herpes virus 1 (HSV1) vector (Kaplitt et al., Molec. Cell. Neurosci. 2:320–330, 1991; International Patent Publication No. WO 94/21807, published Sep. 29, 1994; International Patent Publication No. WO 92/05263, published Apr. 2, 1994).

Adenovirus vectors. Adenoviruses are eukaryotic DNA viruses that can be modified to efficiently deliver a nucleic acid of the invention to a variety of cell types in vivo, and has been used extensively in gene therapy protocols, including for targeting genes to neural cells. Various serotypes of adenovirus exist. Of these serotypes, preference is given to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g., Manhattan or A26/61 strain (ATCC VR-800), for example). Various replication defective adenovirus and minimum adenovirus vectors have been described for gene therapy (WO94/26914, WO95/02697, WO94/28938, WO94/28152, WO94/12649, WO95/02697 WO96/22378). The replication defective recombinant adenoviruses according to the invention can be prepared by any technique known to the person skilled in the art (Levrero et al., Gene 101:195 1991; EP 185 573; Graham, EMBO J. 3:2917, 1984; Graham et al., J. Gen. Virol. 36:59 1977). Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764, Temin et al., U.S. Pat. No. 4,980,289; Markowitz et al., 1988, J. Virol. 62:1120; Temin et al., U.S. Pat. No. 5,124,263, EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al., and Kuo et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as MoMuLV ("murine Moloney leukemia virus"), MEV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAm-12 cell line (WO 89/07150). In addition, the recombinant retroviral vectors can contain modifications within the LTRs for suppressing transcriptional activity as well as extensive encapsidation sequences which may include a part of the gag gene (Bender et al., J. Virol. 61:1639, 1987). Recombinant retroviral vectors are purified by standard techniques known to those having ordinary skill in the art.

Retrovirus vectors can also be introduced by recombinant DNA viruses, which permits one cycle of retroviral replication and amplifies transfection efficiency (see WO 95/22617, WO 95/26411, WO 96/39036, WO 97/19182).

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and non-dividing cells in these tissues, and maintain long-term expression of the gene of interest. For a review, see, Naldini, Curr. Opin. Biotechnol., 9:457–63, 1998; see also Zufferey, et al., J. Virol., 72:9873–80, 1998). Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days (Kafri, et al., J. Virol., 73: 576–584, 1999). The vector produced by the inducible cell line can be concentrated as needed for efficiently transducing nondividing cells in vitro and in vivo.

Non-viral vectors. A vector can be introduced in vivo in a non-viral vector, e.g., by lipofection, with other transfection facilitating agents (peptides, polymers, etc.), or as naked DNA Synthetic cationic lipids can be used to prepare liposomes for in vivo transfection, with targeting in some instances (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g. International Patent Publication WO95/21931), peptides derived from DNA binding proteins (e.g., International Patent Publication WO96/25508), or a cationic polymer (e.g., International Patent Publication WO95/21931). Recently, a relatively low voltage, high efficiency in vivo DNA transfer technique, termed electrotransfer, has been described (Mir et al., C.P. Acad. Sci., 321:893, 1998; WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal.

EXAMPLES

The present invention will be further understood by reference to the following examples, which are provided as exemplary of the invention and not by way of limitation.

Example 1

A Novel PAMP that Mediates βAPP Processing and Notch/Clp1 Signal Transduction

This example shows that both PS1 and PS2 interact with a novel Type I transmembrane protein, PAMP, and that this novel protein also interacts with α- and β-secretase derived fragments of βAPP. We also show that abolition of functional expression of the C. elegans homologue of the protein leads to a developmental phenotype (anterior pharynx 2-aph2) which is thought to be due to inhibition of the glp/Notch signaling pathway. This novel protein is therefore positioned to mediate both the gain of function and loss of function phenotypes associated with presenilin missense mutations and presenilin knockouts, respectively.

Materials and Methods

Antibodies against PS1, PS2 and βAPP. An antibody, termed 1142, directed against PS1, was raised to a peptide segment corresponding to residues 30–45 of PS1 (Levesque et al., J Neurochem 1998: 72:999–1008; Yu et al., Biol Chem 1998; 273:16470–16475). The peptide was synthesized by solid-phase techniques and purified by reverse phase high pressure liquid chromatography (HPLC). Peptide antigens were linked to keyhole limpet hemocyanin (KLH) and used, in combination with complete Freud's adjuvant, to innoculate New Zealand White rabbits. Antisera from three rabbits was pooled, ammonium precipitated and the antibody was purified with Sulfo-link (Pierce) agarose-peptide affinity columns. Other antibodies used include antibody 369, a polyclonal rabbit-anti-human antibody directed against the C-terminus of human βAPP (Buxbaum et al., Proc. Natl. Acad. Sci. USA 1990; 87: 6003–6007); antibody 14 (Ab14), a rabbit polyclonal antibody raised against residues 1–25 of human PS1 (Seeger et al., Proc. Natl. Acad. Sci. 1997, 94: 5090–5094); antibody α-PS1-CTF, a polyclonal rabbit antibody directed against the PS1 loop; and antibody DT2, a monoclonal antibody raised to a GST-fusion protein containing the PS2 N-terminal sequence from residues 1–87.

Preparation of presenilin associated components. To identify membrane associated components of the presenilin complex, an immunoaffinity procedure was used to extract PS1 and tightly associated membrane proteins from semi-purified intracellular membrane fractions. Human embryonic kidney cells (HEK) 293 (ATCC) with a stable over-expression of moderate level wild type human PS1, were grown to confluence, washed twice with ice-cold phosphate-buffered saline, and then homogenized with Buffer A (0.25 M sucrose, 20 mM HEPES pH 7.2, 2 mM EGTA, 2 mM EDTA, 1 mM DTT, and a protease inhibitor cocktail containing 5 $\mu$ml each of Leupeptin, Antipain, pepstatin A, Chymostin, E64, Aprotinin, and 60 $\mu$g/ml 4-(2-aminoethyl)-benzenesulfonyl fluoride (AEBSF)). The cell homogenates were centrifuged 1000×g for 10 minutes to remove cell debris. The supernatant was then centrifuged 10,000×g for 60 minutes. The resulting membrane pellet was resuspended in Buffer B (20 mM HEPES pH 7.2, 1 M KCl, 2 mM EGTA, 2 mM EDTA, 1 mM DTT, and protease inhibitor cocktail as above) and incubated for 45 minutes with agitation at 4° C. Cell membranes were collected again by centrifugation at 107,000×g for 60 minutes. The cell membranes were then lysed on ice for 60 minutes with Buffer C (1% Digitonin, 20 mM HEPES pH 7.2, 100 mM KCl, 2 mM EGTA, 2 mM EDTA, 1 mM DTT, and protease inhibitors cocktail). After spinning 10,000×g for 15 minutes, the protein extract was adjusted with Buffer C to contain 5 mg/ml protein. A total of 0.5 g of protein was obtained.

Isolation. The extracted proteins were then subjected to fractionation with 10–40% glycerol gradient containing 0.5% Digitonin as described (Yu G, et al., J Biol Chem 1998; 273: 16470–16475). After being verified by Western blotting with anti-PS1 antibodies, the peak fractions containing PS1 were pooled and incubated overnight with Protein A/G agarose coupled with either antibody 1142 or a control IgG purified from preimmune rabbit serum. The Protein A/G agarose beads were washed three times with Buffer D (1% Digitonin, 20 mM HEPES pH 7.2, 100 mM KCl, protease inhibitors cocktail), and three times with Buffer E (0.5% Digitonin, 0.5% CHAPS, 20 mM HEPES pH 7.2, 100 mM KCl, 10 mM $CaCl_2$, 5 mM $MgCl_2$, and the protease inhibitor cocktail as above). Isolated protein complexes were eluted from the beads with 0.1M Glycine-HCl, pH 3.0, and then neutralized with 1M Tris. Proteins were then separated by Tris-Glycine SDS-PAGE gels and stained with silver stain and Coomassie Blue stain. The staining of the immuno-purified proteins displayed two intense bands in addition to those of the presenilin holoprotein and its fragments.

Sequence analysis. Individual protein bands were cut out and analyzed with solid-phase extraction capillary electrophoresis mass spectrometry/mass spectrometry (SPE-CE-MS/MS). Briefly, protein bands were first digested in-gel with trypsin; the digested proteins were extracted and dried in a speed vacuum down to concentrate the peptides; and the peptides thereafter separated with micro LC and analyzed by on-line tandem mass spectrometry (Figeys et al., Anal Chem 1999; 71: 2279–2287). Nucleotide and amino acid sequence homology searches were conducted using the BLAST algorithm, and motif analyses performed using the program BLOCKS.

General transfection and analysis methods. Based on the human PAMP sequence, public databases (e.g., GenBank; www.ncbi.nlm.nih.gov) were searched for homologous ESTs (SEQ ID NOs: 3–10), which were collected into a few contigs. These contigs all turned out to be correct, but did not cover full-length mouse and D. melanogaster cDNAs.

Full length murine (SEQ ID NO: 15), human (SEQ ID NO: 13) and D. melanogaster (SEQ ID NO: 17) PAMP cDNAs were obtained using oligonucleotides designed from partial cDNA/EST sequences in public databases to screen appropriate cDNA libraries, for 5'RACE, and/or for RT-PCR experiments. A PAMP expression construct was generated by inserting human PAMP cDNA in-frame with the V5 epitope of pcDNA6 (Invitrogen) at the C-terminus of PAMP. HEK293 cells with a stable expression of PS1/PS2 and $\beta APP_{sw}$ were transiently transfected with either V5-tagged PAMP or empty plasmid (mock transfection control). Duplicate experiments were performed by: (1) transient transfection of V5-PAMP and $\beta APP_{695}$ (or empty vector plus $\beta APP_{695}$ as a mock transfection control) into murine embryonic fibroblasts stably infected with human PS1 expressed from a retroviral vector construct (Clontech, CA); or (2) transient transfection of V5-PAMP (or an empty plasmid) into HEK293 cell lines with a stable expression of the C-terminal 99 amino acids of βAPP with a preceding artificial signal peptide (spC100-APP) together with either wild type PS1, PS1-L392V, or PS1-D385A. Cells were lysed with a Digitonin lysis buffer or with 1% NP40, and the protein extracts were subjected to gradient fraction, immunoprecipitation or direct Western blotting as described (Yu G, et al., J Biol Chem 1998; 273: 16470–16475). PS1 was immunodetected or immunoprecipitated with antibodies 14 or α-PS1-CTF; and PS2 was immunodetected or immunoprecipitated with antibody DT2. FL-βAPP and its C-terminal α- and β-secretase derivatives were detected using antibody 369.

Results

Isolation of PAMP. Immunoprecipitation of PS1 protein complexes, followed by SDS-PAGE with Coomassie Blue and silver staining, yielded two intense bands in addition to presenilin holoprotein. These bands were characterized by mass spectroscopy analysis. Mass spectroscopy analysis revealed several armadillo repeat containing peptides, (previously known to functionally interact with presenilins (Yu G, et al., J Biol Chem 1998; 273–16470–16475.; Zhou J, et al., NeuroReport (Fast Track) 1997; 8: 2085–2090; Nishimura M, et al., Nature Med 1999; 5: 164–169), and a novel peptide (AMP) which had a sequence identified to that predicted for an anonymous, partial cDNA (Genbank; Accession No. D87442). The cDNA sequence predicted an open reading frame of 709 amino acids (SEQ ID NO: 14), which contains a putative N-terminal signal peptide, a long N-terminal hydrophilic domain with sequence motifs for glycosylation, N-myristoylation and phosphorylation, a ~20 residue hydrophobic putative transmembrane domain, and a short hydrophilic C-terminus of 20 residues (FIGS. 1A and 1B).

Orthologous PAMP proteins. The PAMP amino acid sequence had no significant homology to other proteins within available databases, except for a hypothetical C.elegans protein (www.ncbi.nih.gov; Accession No. Q23316) ($p=2\times10^{-28}$; identity=22%; similarity=39%) (SEQ ID NO: 12) ascertained from a genomic DNA sequence (FIGS. 1A and 1B). In addition to strong primary amino acid sequence conservation, this C.elegans protein has a very similar topology to human PAMP, suggesting that it is the nematode orthologue of human PAMP.

In the absence of functional clues arising from homologies to other known proteins, the predicted amino acid sequences of the murine (SEQ ID NO: 16) and D.melanogaster (SEQ ID NO: 18) orthologues of PAMP were cloned and examined. The four orthologous PAMP proteins had a similar topology and significant sequence conservation near residues 306–360, 419–458, and 625–662 of human PAMP (SEQ ID NO: 14) (FIGS. 1A and 1B). Motif analysis of these conserved domains revealed a weak similarity (strength=1046) between residues 625–641 (ARLARALSPAFELSQWS; SEQ ID NO: 19) of mouse and human PAMP to cyclic nucleotide binding domains While the putative transmembrane domain sequences were not highly conserved, all four orthologues contained a conserved serine residue within this hydrophobic domain. Finally, there were four conserved cysteine residues in the—terminal hydrophilic domain ($Cys_{195}$, $Cys_{213}$, $Cys_{230}$, and $Cys_{248}$ in human PAMP) which had a periodicity of 16–17 residues in the N-terminus, and may form a functional domain (e.g., a metal binding domain or disulfide bridges for stabilizing the tertiary structure of PAMP/PAMP complexes).

Interaction of PAMP with presenilin 1. To confirm the authenticity of the PAMP:PS1 interaction, HEK293 cells were transiently transfected with PAMP cDNA (SEQ ID NO: 13) tagged at the 3'-end with a V5-epitope encoded from the pcDNA6 vector. The conditioned media were collected 20 hr after transient transfection with PAMP (or with empty vector), and the $A\beta_{40}$ and $A\beta_{42}$ levels were measured by ELISA (Zhang L, et al., J Biol Chem 1999; 274: 8966–8972.). In Western blots of lysates of these cells, the use of anti-V5 (Invitrogen, CA) and enhanced chemiluminescence (Amersham) detected a V5-immunoreactive band of ~110 kDa which was reduced to ~80 kDa following Endo H digestion (equivalent to the size predicted from the PAMP amino acid sequence), confirming the predicted glycosylation of PAMP. In addition, a series of about 7–10 kDa fragments were observed, which are predicted to contain the TM domain and short C-terminus of PAS plus the 3 kDa V5-epitope. These C-terminal derivatives may be authentic cleavage products of full-length PAMP, or, alternatively, a proteolytic artifact arising from the attachment of the V5-epitope to the C-terminus of PAMP.

Reciprocal immunoprecipitation studies in cells expressing combinations of transfected V5-tagged-PAMP, transfected wild type or mutant PS1, transfected wild type PS2, or endogenous presenilins, confirmed the PS1:PAMP interaction, and showed a similar interaction between PAMP and PS2. In contrast, immunoprecipitation of other ER-resident proteins (e.g., calnexin) failed to show any evidence of an interaction between these proteins and PAMP. Glycerol velocity gradient analysis of the native conformation of PAMP revealed that PAMP was co-eluted into the same high molecular weight fractions as PS1 and PS2, indicating that it is an authentic component of the high molecular weight presenilin protein complexes. These biochemical data were supported by immunocytochemical studies, which showed that transfected PAMP and endogenous PS1 strongly co-localized in the ER and Golgi in MDCK canine kidney/epithelial cells (ATCC). Similar studies with PS2 confirmed that PAMP also tightly associates with both endogenous PS2 in human brain and with transfected PS2 in HEK293 cells.

The PAMP gene. Chromosomal locations and genetic map positions of the murine and human PAMPS were obtained, from public genetic and transcriptional maps (World Wide Web (www) ncbi.nlm.nih.gov). The gene encoding PAMP is located on human chromosome 1 near the genetic markers D1S1595 and D1S2844. The 5'-end of the PAMP gene is embedded in the 5'-end of the coatmer gene encoded on the opposite strand. The human PAMP gene is close to a cluster of markers which have yielded positive, but sub-significant evidence for linkage to or association with Alzheimer Disease in two independent genome wide surveys (Kehoe P, et al. Hum Mol Genet 1999; 8: 237–245). The murine PAMP maps within a 700 Kb interval of murine chromosome 1 which contains the gene defect associated with Looptail phenotype in mice (Underhill D A, et al., Genomics 1999; 55: 185–193). Mice heterozygous for Looptail show developmental defects in dorsal axial structures including notochord, brain, spinal cord, and somites (Greene N D, et al., Mech Dev 1998; 73: 59–72.), which are reminiscent of those observed in PS1-/- mice (Shen J, et al., Cell 1997; 89; 629–639; Wong P C, et al., Nature 1997; 387:288–292). These observations suggest that the presenilin; PAMP complex may be involved in both βAPP and Notch processing.

C. elegans homolog of PAMP. The C. elegans homolog of PAMP corresponds to the aph-2 gene. Mutations in aph-2 have been identified in a screen for mutants with phenotypes identical to embryonic mutant phenotypes caused by loss of glp-l activity, i.e., lack of an anterior pharynx, e.g. cDNA clone. The EST corresponding to aph-2, (cDNA clone yk477b8, kindly provided by Y. Kohara, National Institute of Genetics, Japan) was sequenced and the coding region (SEQ ID NO: 11) found to match exactly the Genefinder prediction made by the C. elegans sequencing consortium (Genbank; Accession No. Z75714). Double stranded RNA interference (RNAi) confirmed the mutant phenotype of aph-2. Sense and antisense RNA were transcribed in vitro from PCR product amplified from the phage yk477b8. After annealing equal quantities of sense and antisense products, the dsRNA product made was injected into L4 stage wild-type worms. The chosen line of worms, designated lin-12 (n302) (Greenwald and Seydoux, Nature 1990: 346:197–199, Greenwald, et al., Cell 1983: 34; 435–444) was obtained from the Caenorhabditis Genetics Center. Injected animals were transferred to fresh plates daily and the progeny scored at least 36 hours alter injection for the embryonic lethal phenotype and 4–5 days after injection for the egg-laying phenotypes. Animals injected with dsRNA from yk477b8 template produced eggs that lacked an anterior pharynx. These results support the notion that aph-2/PAMP contributes to cell interactions mediated by glp-l/Notch in the embryo.

Functional role for the PAMP: presenilin complexes in βAPP processing. To examine a functional role for the PAMP: presenilin complexes in βAPP processing, the interactions between PAMP, PS1, and βAPP, and its derivatives were investigated. The cell lines used were transiently transfected with V5-tagged PAMP, and stably expressing wild type $\beta APP_{695}$ in addition to wild type PS1, wild type PS2, PS1-L392V mutant, or PS1-D385A mutant. The PS1-L392V mutation is a pathogenic mutation associated with familial AD (Sherrington R, et al., Nature 1995; 375:754–760) and with increased secretion of $A\beta_{42}$ (Scheuner D, et al. Nature Med 1996; 2:864–870, Citron M, et al. Nature Med 1997; 3:67–72). The PS1-D385A mutation is a loss of function mutation associated with inhibition of PS1 endoproteolysis and a decrease in γ-secretase activity (Wolfe M S, et al., Nature 1999; 398: 513–517). The conditioned media were collected 20 hr after transient transfection with PAMP (or with empty vector), and the $A\beta_{40}$ and $A\beta_{42}$ levels were measured by ELISA (Zhang L, et al., J Biol Chem 1999; 274: 8966–8972). Analysis of Western blots from these co-immunoprecipitation experiments revealed that PAMP holoprotein (and C-terminally tagged proteolytic fragments of PAMP) interacted in equivalent degrees with wild type PS1, wild type PS2, PS1-L392V mutant, and PS1-D385A mutant proteins. In addition, PAMP holoprotein and the C-terminal proteolytic fragments of PAMP also co-immunoprecipitated with the C-terminal proteolytic fragments of βAPP but not βAPP holoprotein in lysates of cells expressing either βAPP holoprotein or just the C-terminal 99 amino acids of βAPP. Significantly, compared to cells expressing equivalent quantities of wild type PS1, cell lines expressing pathogenic mutations of PS1 showed increased amounts of C-terminal βAPP fragments co-immunoprecipitating with PAMP. Conversely, cell lines expressing the loss-of-function PS1-D385A mutation showed greatly reduced amounts of C-terminal βAPP derivatives co-immunoprecipitating with PAMP despite the presence of very large amounts of C-terminal βAPP derivatives in these cells.

These results were confirmed in HEK293 cells overexpressing either $\beta APP_{Swedish}$ or the SpC99-βAPP cDNA.

The latter encodes the C-terminal 99 residues of βAPP (corresponding to the products of β-secretase cleavage) plus the βAPP signal peptide. The interaction of PAMP appears much stronger with C99-βAPP than that with C83-βAPP. However, C83-βAPP is much less abundant in these cells. In fact, PAMP does interact with both C99- and C83-βAPP stubs. Cumulatively, these results indicate that PAMP likely interacts with the C-terminal derivatives of βAPP which are the immediate precursors of Aβ and p3. However, of greater interest, the genotype of the co-expressed PS1 molecule dynamically influenced the interaction between PAMP and C99-/C83-βAPP stubs. Thus, more C-terminal βAPP fragments co-immunoprecipitated with PAMP in cells expressing the FAD-associated PS1-L392V mutation compared to cells expressing wild type PS1 (and equivalent quantities of nicastrin and C99-βAPP). Conversely, much less C-terminal βAPP derivatives co-immunoprecipitated with PAMP in cell lines expressing the loss-of-function PS1-D385A mutation (despite the presence of very large amounts of C-terminal βAPP derivatives in these cells). These effects are more easily seen in cells over-expressing the C99-βAPP construct. However, similar but less pronounced differences were also observed in cells over-expressing full-length $βAPP_{Swedish}$. More importantly, the PS1-sequence-related differences in the interaction of PAMP with C-terminal βAPP derivatives were most evident within 24 hours of transient transfection of PAMP. By 72 hours, the PS1-sequence-related differences were largely abolished. This dynamic change in the interaction of PAMP with C99/C83-βAPP was not due to changes in the levels of PS1, C-terminal βAPP derivatives or PAMP. One interpretation of these results is that the presenilins may be dynamically involved in regulating or loading PAMP with the substrates of β-secretase.

Presenilin binding domains of PAMP. In transiently transfected cells (in which the 7–10 kDa C-terminal of PAMP can be detected), anti-PS1 immunoprecipitation products contain both full length PAMP and the ~7–10 kDa C-terminal PAMP fragments. Similarly, in these cells, immunoprecipitation with antibodies to the C-terminus of βAPP (Ab369) also renders C-terminal nicastrin epitopes. The TM domain of PAMP is not highly conserved in evolution. These results suggest that the C99-/C83-βAPP and PS1/PS2-binding domain(s) of PAMP are in the TM domain or C-terminus.

Discussion

The above results indicate that PAMP is a component of the PS1 and PS2 intracellular complexes. The observations that PAMP also binds to the C-terminal fragment of βAPP (arising from α- and β-secretase cleavage of full length βAPP), that the degree of binding of these fragments to PAMP is modulated by mutations in PS1, and that the direction of this modulation is congruent with the effects of each mutant of Aβ production (i.e., the pathogenic L392V mutation increases binding to PAMP and increases $Aβ_{42}$ production whereas the D385A mutation has the opposite effects) strongly argues that PAMP is part of a functional complex involved in processing of C-terminal βAPP derivatives. Similarly, the observation that inhibition of PAMP expression in *C. elegans* leads to a phenotype similar to that of glp/Notch loss of function, argues that PAMP, like PS1 and PS2, is also a functional component of the pathways involved in processing of Notch. This conclusion is strengthened by the fact that the murine PAMP gene maps within a 700 kb interval on murine chromosome 1 which carries the Looptail mutant, and is thus likely to be the site of the Looptail mutation. Looptail has a number of phenotypic similarities to those of Notch and PS1 knockouts in mice. Because Looptail is a model of human spinal cord malformations including spina bifida, PAMP biology may also provide some useful insights into this neurological developmental defect as well.

At the current time the exact role of PAMP in the presenilin-complex-mediated processing of βAPP and Notch-like molecules is not fully defined. Inspection of the primary amino acid sequence of PAMP does not reveal very strong homologies to known proteases. However, the recombinant expression systems of the invention permit evaluation of three-dimensional structure of PAMP; it is possible that PAMP itself has a protease activity. However, it is currently more plausible that PAMP plays another role in βAPP and Notch processing. Thus, PAMP may be involved in the function of PS1 and PS2 complexes by binding substrates for γ-secretase. The efficacy of this binding is clearly modulated by PS1 mutations in a direction which is commensurate with the effect of these mutations on γ-secretase activity. Alternatively, PAMP may have a regulatory role on the activity of the presenilin complexes. This is consistent with the observation that residues 625–641 of human and murine PAMP contain a motif similar to cyclic nucleotide binding domains of several other unrelated proteins.

Regardless of its precise role, it is clear that PAMP and PS1 both play important roles in γ-secretase mediated processing of βAPP. Hence, knowledge of PAMP and its biology will now serve as a target for efforts to manipulate the function of the presenilin complexes in patients with Alzheimer Disease and related disorders, patients with malignancies (in which the presenilins have been implicated by virtue of a role in programmed cell death), and in disorders of development especially of the spinal cord and brain (in view of the known effects of PS1 knockout and the strong likelihood that PAMP is the site of Looptail mutations in mice). In particular, knowledge of the domains of PAMP involved in binding presenilins and βAPP derivatives (which currently appears to be located within the C-terminal transmembrane and hydrophilic domains of PAMP) and the identification of putative ligands interacting with the conserved domains at the hydrophilic N-terminus of PAMP will considerably expedite this goal.

We have found that the strength of the interaction between PAMP and the C-terminal fragments of βAPP (which is the precursor Aβ) is determined by the genotype at PS1. Thus, clinical mutations in PS1 which cause Alzheimer Disease and an increase in the production of $Aβ_{42}$ are associated with increased binding of the C-terminal fragments of βAPP to PAMP. Conversely, loss of function mutations in PS1 (Asp385Ala) which inhibit γ-secretase cleavage of C-terminal fragments of βAPP, are associated with abolition of the interaction between PAMP and the C-terminal fragments of βAPP.

Finally, the apparent C-terminal proteolytic derivatives of PAMP could either be authentic, or simply artefacts due to the V-5 tag. If they are authentic, this observation raises the possibility that PAMP may undergo post-translational processing events which are potentially similar At to those of βAPP and/or Notch. Three observations support our discovery of PAMP. First, in contrast to βAPP and Notch, which are not major constituents of the high molecular weight presenilin complexes, and which can only be inconsistently shown to be directly associated with PS1/PS2, PAMP is a major stoichiometric component of the presenilin complexes. Second, PAMP selectively interacts only with C-terminal derivatives of βAPP which are substrates for γ-secretase cleavage, and this interaction is modulated by PS1 mutations in a way which reflects the functional consequences of these PS1 mutations. Third, inhibition of PAMP expression in *C. elegans* leads to a disease phenotype likely to be in the glp/Notch signaling pathway.

Example 2

PAMP Mutants Useful for Studies on Alzheimer's Disease

Site-directed mutagenesis was used to generate the following artificial mutations in PAMP:
Cys: $PAMP_{C230A}$ in the 4 conserved cystine motif
DYIGS: $PAMP_{D336A/Y337A}$ in the central conserved region
D369L: $PAMP_{\Delta312\text{-}369}$ in the central conserved region
D340X: $PAMP_{\Delta312\text{-}340}$ in the central conserved region
YDT: $PAMP_{D458A}$ in the putative 'aspartyl protease' DTA site
SPAF: $PAMP_{P633A/F635A}$ in the SPAF motif
TM: $PAMP_{S683A}$ in the TM domain
C3D: $PAMP_{\Delta630\text{-}668}$ in the conserved region adjacent to the TM domain To further examine the role of nicastrin in βAPP processing, we inserted PAMP cDNAs, harboring the above mutations as well as normal/wild type PAMP ($PAMP_{wt}$) cDNA and the cDNA for an unrelated protein (LacZ), in frame into pcDNA6 vectors. A series of HEK293 cell lines stably expressing endogenous PS1, $\beta APP_{Swedish}$ and either wild type nicastrin or nicastrin constructs in which various conserved domains had been mutated or deleted, were then created by transfection. PAMP expressing cells were selected with lasticidin to generate stable cell lines. Conditioned media from these cell lines were collected after 6–24 hours and $A\beta_{40}$ and $A\beta_{42}$ were measured by ELISA.

In the $PAMP_{D336A/Y337A}$ mutant, both $A\beta_{40}$ and $A\beta_{42}$ levels were increased, and there was also a 68% increase in $A\beta_{42}/A\beta_{40}$ ratio which is very similar to that observed in clinical mutations in APP, PS1, and PS2, associated with early onset Alzheimer Disease. The $A\beta_{42}/A\beta_{40}$ ratio was also increased in one cell line expressing the $PAMP_{C230A}$ mutant.

In contrast, both the total $A\beta_{42}$ and $A\beta_{40}$ levels and the $A\beta_{42}/A\beta_{40}$ ratio were massively reduced (to only 18% of the control) in the $PAMP_{\Delta312\text{-}369}$ mutant. A similar but less profound reduction of both the total $A\beta_{42}$ and $A\beta_{40}$ levels and the $A\beta_{42}/A\beta_{40}$ ratio was observed in the conditioned medium from the $PAMP_{\Delta312\text{-}340}$ cell lines.

There is no apparent difference in $A\beta_{42}$ or $A\beta_{40}$ levels, or in the $A\beta_{42}/A\beta_{40}$ ratio, when the $PAMP_{wt}$, $PAMP_{D458A}$, $PAMP_{\Delta630\text{-}668}$, $PAMP_{P633A/F635A}$, and $PAMP_{S683A}$ cells were compared to control lines (expressing LacZ, or empty vector).

Thus, certain PAMP mutants cause biochemical changes similar to those induced by mutations in the βAPP, PS1, and PS2 genes which give rise to Alzheimer Disease. These artificial PAMP mutations can therefore be used to generate cellular and other model systems to design treatments and preventions for Alzheimer Disease related disorders. These mutations also show that PAMP is involved in the pathogenesis of AD, and may provide information for the design of specific molecular diagnostics or therapeutics.

When compared to mock-transfected or LacZ transfected cells, overexpression of wild type PAMP, and overexpression of most PAMP mutation- or deletion-constructs had no significant effect on Aβ secretion. However, missense mutation of the conserved DYIGS motif to AAIGS (residues 336–340 of human PAMP) caused a significant increase in $A\beta_{42}$ secretion, a smaller increase in $A\beta_{40}$ secretion, and an increase in the $A\beta_{42}/A\beta_{40}$ ratio ($p<0.001$; Table 2). This increase in $A\beta_{42}$ production was equivalent to that of FAD-related missense mutations in PS1. Conversely, deletion of the DYIGS domain in two independent constructs ($PAMP_{\Delta312\text{-}369}$ and $PAMP_{\Delta312\text{-}340}$) caused a significant reduction in both $A\beta_{42}$ and $A\beta_{40}$ secretion which was more profound in $PAMP_{\Delta312\text{-}369}$ cells than in $PAMP_{\Delta312\text{-}340}$ cells (Table 2). The magnitude of the reduction in Aβ secretion in $PAMP_{\Delta312\text{-}369}$ cells was equivalent to that observed with the PS1-D385A loss-of-function mutation. Somewhat unexpectedly, and in contrast to $PS1^{-/-}$ and PS1-D385A cells, the reduction in Aβ secretion in $NCT_{\Delta312\text{-}369}$ and $NCT_{\Delta312\text{-}340}$ cells was not accompanied by the expected accumulation of C99- and C83-βAPP stubs. Since there was no consistent change in the levels of soluble βAPP ($\beta APP_a$) in the conditioned medium of any of the PAMP mutant cells, the most probable explanation for this result is that C99- and C83-βAPP stubs which do not enter the PAMP:presenilin complex for γ-secretase cleavage to Aβ may be degraded by other pathways.

The effects of PAMP mutations on Aβ secretion were not due to trivial explanations such as differences in the levels of PAMP, βAPP holoprotein, or PS1/PS2. None of these mutations caused any consistent, detectable change in the amount of $APP_a$ in conditioned medium or in the amount of C99/C83-βAPP that could be co-immunoprecipitated with PAMP. However, both the $PAMP_{\Delta312\text{-}369}$ mutant and the $PAMP_{\Delta312\text{-}340}$ deletion mutant significantly reduced the amount of PS1 which could be co-immunoprecipitated with PAMP. Interestingly, the reduction in efficiency of binding to PS1 was proportional to the reduction in Aβ secretion induced by each deletion mutant. Multiple mechanisms underlying the effect of mutations in the first conserved domain can explain these results. This domain contains no obvious functional motifs (e.g., for glycosylation etc.), nor does it have significant sequence homology to other known proteins. Consequently, the three functionally active PAMP mutations either affect a presenilin-binding domain in PAMP, or affect a specific regulatory domain of PAMP which modulates both direct binding of PAMP to PS1 and the subsequent γ-secretase-mediated cleavage of PAMP-bound C99- and C83-βAPP stubs.

TABLE 2

| Transfection | Normalized $A\beta_{42}$ | Normalized $A\beta_{40}$ | $A\beta_{42}/A\beta_{40}$ Ratio |
|---|---|---|---|
| Mock (LacZ/empty vector) | 1.0 | 1.0 | 1.0 |
| wild type PAMP | 1.03 ± 0.09 | 1.05 ± 0.07 | 0.99 ± 0.07 |
| D336A/Y337A | 3.09 ± 0.59 ($p < 0.001$) | 1.61 ± 0.19 ($p = 0.001$) | 1.81 ± 0.15 ($p < 0.001$) |
| $PAMP_{\Delta312\text{–}369}$ | 0.05 ± 0.04 ($p < 0.001$) | 0.31 ± 0.06 ($p < 0.001$) | 0.09 ± 0.05 ($p < 0.001$) |
| $PAMP_{\Delta312\text{–}340}$ | 0.33 ± 0.04 ($p = 0.002$) | 0.55 ± 0.04 ($p = 0.001$) | 0.59 ± 0.06 ($p = 0.003$) |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, and publications are cited throughout this application, the disclosures of which are incorporated herein by reference in their entireties.

We claim:

1. An isolated nucleic acid which encodes human presenilin-associated membrane protein (PAMP) as set forth in SEQ ID NO:14.

2. The isolated nucleic acid of claim 1 which comprises a nucleotide sequence encoding human PAMP as set forth in SEQ ID NO:13.

3. A vector comprising the nucleic acid of claim 1 operatively associated with an expression control sequence.

4. An isolated cell comprising the vector of claim 3.

5. A method for producing human PAMP, which method comprises culturing the cell of claim 4 under conditions treat permit expression of the human PAMP.

6. An isolated nucleic acid encoding a mutant PAMP, wherein the mutant PAMP has a mutation in an amino acid residue corresponding to an amino acid selected from the group consisting of C230, D336, Y337, and both D336 and Y337, of human PAMP as set forth in SEQ ID NO:14.

7. The isolated nucleic acid of claim 6, wherein the mutation is selected from the group consisting of C230A, D336A, Y337A, and both D336A and Y337A.

8. A vector comprising the nucleic acid of claim 6, operatively associated with an expression control sequence.

9. An isolated call transfected with the vector of claim 8.

10. A method for producing a mutant of SEQ ID NO:14, which method comprises culturing the cell of claim 9 under conditions that permit expression of the mutant PAMP.

11. An isolated nucleic acid encoding a mutant human PAMP less capable than human PAMP as set forth in SEQ ID NO:14 of interacting with a presenilin protein, wherein the mutant PAMP has a deletion of an amino acid sequence corresponding to Δ312–369 of Δ312–340 of SEQ ID NO:14.

12. A vector comprising the nucleic acid of claim 11, operatively associated with an expression control sequence.

13. An isolated cell transfected with the vector of claim 12.

14. A method for producing a mutant of SEQ ID NO:14, which method comprises culturing the cell of claim 13 under conditions that permit expression of the mutant PAMP.

* * * * *